(12) United States Patent
Chen et al.

(10) Patent No.: US 7,575,863 B2
(45) Date of Patent: Aug. 18, 2009

(54) METHODS, COMPOSITIONS, AND KITS COMPRISING LINKER PROBES FOR QUANTIFYING POLYNUCLEOTIDES

(75) Inventors: Caifu Chen, Palo Alto, CA (US); Dana Ridzon, San Ramon, CA (US); Zhaohui Zhou, Fremont, CA (US); Kai Qin Lao, Pleasanton, CA (US); Neil A. Straus, Emeryville, CA (US)

(73) Assignee: Applied Biosystems, LLC, Carlsbad, CA (US)

( * ) Notice: Subject to any disclaimer, the term of this patent is extended or adjusted under 35 U.S.C. 154(b) by 0 days.

(21) Appl. No.: 10/947,460

(22) Filed: Sep. 21, 2004

(65) Prior Publication Data

US 2005/0266418 A1    Dec. 1, 2005

Related U.S. Application Data

(60) Provisional application No. 60/575,661, filed on May 28, 2004.

(51) Int. Cl.
C12Q 1/68 (2006.01)
C12P 19/34 (2006.01)

(52) U.S. Cl. .......................................... 435/6; 435/91.2
(58) Field of Classification Search ........................ None
See application file for complete search history.

(56) References Cited

U.S. PATENT DOCUMENTS

| | | | |
|---|---|---|---|
| 4,683,202 A | 7/1987 | Mullis | |
| 4,800,159 A | 1/1989 | Mullis et al. | |
| 5,210,015 A | 5/1993 | Gelfand et al. | |
| 5,538,848 A | 7/1996 | Livak et al. | |
| 5,874,260 A | 2/1999 | Cleuziat et al. | |
| 5,876,930 A | 3/1999 | Livak et al. | |
| 5,952,202 A | 9/1999 | Aoyagi et al. | |
| 6,030,787 A | 2/2000 | Livak et al. | |
| 6,037,130 A | 3/2000 | Tyagi et al. | |
| 6,040,166 A | 3/2000 | Erlich et al. | |
| 6,090,557 A * | 7/2000 | Weiss | 435/6 |
| 6,114,152 A | 9/2000 | Serafini et al. | |
| 6,117,635 A * | 9/2000 | Nazarenko et al. | 435/6 |
| 6,197,563 B1 | 3/2001 | Erlich et al. | |
| 6,258,569 B1 | 7/2001 | Livak et al. | |
| 6,270,967 B1 | 8/2001 | Whitcombe et al. | |
| 6,358,679 B1 | 3/2002 | Heid et al. | |
| 6,403,319 B1 | 6/2002 | Lizardi et al. | |
| 6,498,025 B1 | 12/2002 | Miller | |
| 6,582,936 B1 | 6/2003 | Serafini et al. | |
| 6,605,451 B1 | 8/2003 | Marmaro et al. | |
| 6,692,915 B1 | 2/2004 | Nallur | |
| 6,764,821 B1 | 7/2004 | Rabbani et al. | |
| 6,821,727 B1 | 11/2004 | Livak et al. | |
| 6,884,583 B2 | 4/2005 | Livak et al. | |
| 2003/0235854 A1* | 12/2003 | Chan et al. | 435/6 |
| 2004/0175732 A1* | 9/2004 | Rana | 435/6 |
| 2004/0214196 A1 | 10/2004 | Aydin et al. | |
| 2005/0059049 A1* | 3/2005 | Moen et al. | 435/6 |
| 2005/0260640 A1 | 11/2005 | Andersen et al. | |
| 2005/0266418 A1 | 12/2005 | Chen et al. | |
| 2005/0272071 A1 | 12/2005 | Lao et al. | |
| 2006/0035215 A9 | 2/2006 | Sorge et al. | |
| 2006/0035217 A1* | 2/2006 | Livak et al. | 435/6 |
| 2006/0057595 A1 | 3/2006 | Lao et al. | |
| 2006/0063163 A1 | 3/2006 | Chen et al. | |
| 2006/0078924 A1 | 4/2006 | Finn et al. | |
| 2006/0194225 A1 | 8/2006 | Spier | |
| 2007/0015176 A1 | 1/2007 | Lao et al. | |
| 2007/0048757 A1 | 3/2007 | Lao et al. | |
| 2007/0111226 A1 | 5/2007 | Tan et al. | |

FOREIGN PATENT DOCUMENTS

| | | |
|---|---|---|
| WO | WO 00/79009 A2 | 12/2000 |
| WO | WO 02/061143 A2 | 8/2002 |
| WO | WO 2004/022784 A2 | 3/2004 |

OTHER PUBLICATIONS

Brennecke et al. Towards a complete description of the microRNA complement of animal genomes. Genome Biology 2003, vol. 4, pp. 228.1-228.3.

Chen et al., "Real-time PCR: Advancing RNA Interference and MicroRNA Studies" Pharmaceutical Discovery Online, May 1, 2005, pp. 1-5.

International Search Report and Written Opinion mailed Feb. 21, 2006 issued in International Application No. PCT/US2005/033943, 14 pages.

(Continued)

*Primary Examiner*—Kenneth R. Horlick
*Assistant Examiner*—David C Thomas
(74) *Attorney, Agent, or Firm*—Life Technologies Corp.

(57) ABSTRACT

The present invention is directed to methods, reagents, kits, and compositions for identifying and quantifying target polynucleotide sequences. A linker probe comprising a 3' target specific portion, a loop, and a stem is hybridized to a target polynucleotide and extended to form a reaction product that includes a reverse primer portion and the stem nucleotides. A detector probe, a specific forward primer, and a reverse primer can be employed in an amplification reaction wherein the detector probe can detect the amplified target polynucleotide based on the stem nucleotides introduced by the linker probe. In some embodiments a plurality of short miRNAs are queried with a plurality of linker probes, wherein the linker probes all comprise a universal reverse primer portion a different 3' target specific portion and different stems. The plurality of queried miRNAs can then be decoded in a plurality of amplification reactions.

104 Claims, 6 Drawing Sheets

OTHER PUBLICATIONS

Guegler et al., "Quantitation of Plant miRNAs by RT-PCR" published online, 2005, publication from Applied Biosystems website, URL: http://docs.appliedbiosystems.com, retrieved on Feb. 2, 2006, 1 page.
U.S. Appl. No. 10/944,153, filed Sep. 16, 2004.
U.S. Appl. No. 60/711,480, filed Aug. 24, 2005.
U.S. Appl. No. 60/750,302, filed Dec. 13, 2005.
File History of U.S. Appl. No. 11/142,720, filed May 31, 2005.
File History of U.S. Appl. No. 11/232,475, filed Sep. 21, 2005.

* cited by examiner

FIG. 2
(A) 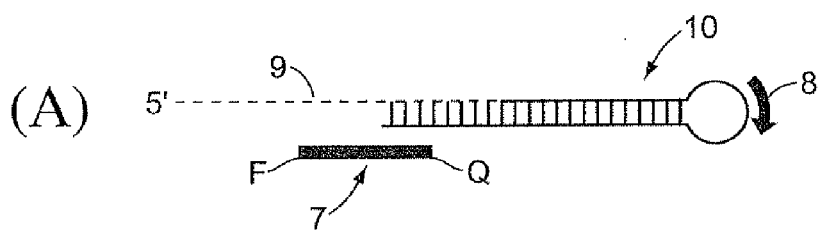
(B) 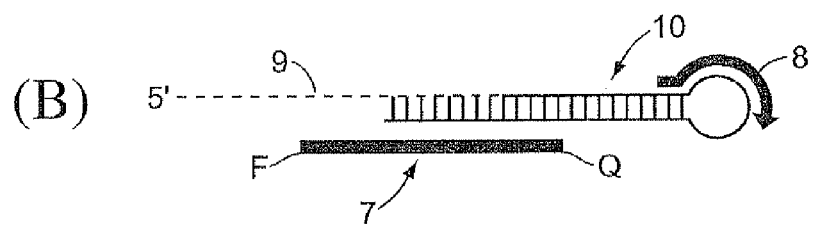
(C) 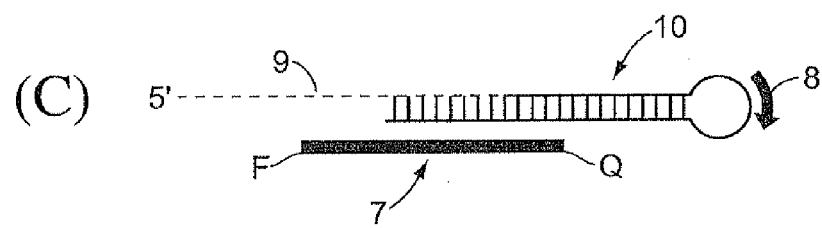
(D) 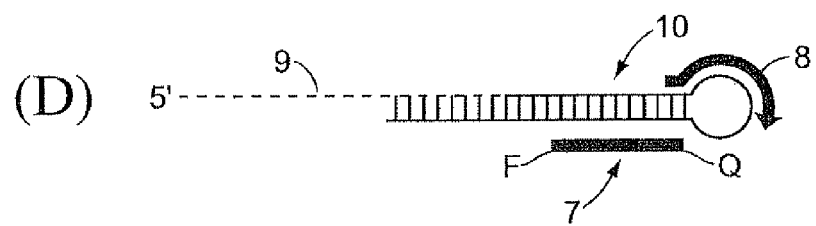

METHODS, COMPOSITIONS, AND KITS COMPRISING LINKER PROBES FOR QUANTIFYING POLYNUCLEOTIDES

RELATED APPLICATIONS

This application claims priority to U.S. Provisional Application 60/575,661, filed May 28, 2004, for "Methods, Compositions, and Kits for Quantifying Target Polynucleotides" by Chen and Zhou.

FIELD

The present teachings are in the field of molecular and cell biology, specifically in the field of detecting target polynucleotides such as miRNA.

INTRODUCTION

RNA interference (RNAi) is a highly coordinated, sequence-specific mechanism involved in posttranscriptional gene regulation. During the initial steps of process, a ribonuclease (RNase) II-like enzyme called Dicer reduces long double-strand RNA (dsRNA) and complex hairpin precursors into: 1) small interfering RNAs (siRNA) that degrade messenger RNA (mRNA) and 2) micro RNAs (miRNAs) that can target mRNAs for cleavage or attenuate translation.

The siRNA class of molecules is thought to be comprised of 21-23 nucleotide (nt) duplexes with characteristic dinucleotide 3' overhangs (Ambros et al., 2003, RNA, 9 (3), 277-279). siRNA has been shown to act as the functional intermediate in RNAi, specifically directing cleavage of complementary mRNA targets in a process that is commonly regarded to be an antiviral cellular defense mechanism (Elbashir et al., 2001, Nature, 411:6836), 494-498, Elbashir et al., 2001, Genes and Development, 15 (2), 188-200). Target RNA cleavage is catalyzed by the RNA-induced silencing complex (RISC), which functions as a siRNA directed endonuclease (reviewed in Bartel, 2004, Cell, 116 (2), 281-297).

Micro RNAs (miRNAs) typically comprise single-stranded, endogenous oligoribonucleotides of roughly 22 (18-25) bases in length that are processed from larger stem-looped precursor RNAs. The first genes recognized to encode miRNAs, lin-4 and let-7 of *C. elegans*, were identified on the basis of the developmental timing defects associated with the loss-of-function mutations (Lee et al., 1993, Cell, 75 (5), 843-854; Reinhart et al., 2000, Nature, 403, (6772), 901-906; reviewed by Pasquinell; et al., 2002, Annual Review of Cell and Developmental Biology, 18, 495-513). The breadth and importance of miRNA-directed gene regulation are coming into focus as more miRNAs and regulatory targets and functions are discovered. To date, a total of at least 700 miRNAs have been identified in *C. elegans, Drosophila* (Fire et al., 1998, Nature, 391 (6669), 805-811), mouse, human (Lagos-Quintana et al., 2001, Science, 294 (5543), 853-858), and plants (Reinhart et al., 2002, Genes and Development, 16 (13), 1616-1626). Their sequences are typically conserved among different species. Size ranges from 18 to 25 nucleotides for miRNAs are the most commonly observed to date.

The function of most miRNAs is not known. Recently discovered miRNA functions include control of cell proliferation, cell death, and fat metabolism in flies (Brennecke et al., 2003, cell, 113 (1), 25-36; Xu et al, 2003, Current Biology, 13 (9), 790-795), neuronal patterning in nematodes (Johnston and Hobert, 2003, Nature, 426 (6968), 845-849), modulation of hematopoietic lineage differentiation in mammals (Chen et al., 2004, Science, 303 (5654), 83-87), and control of leaf and flower development in plants (Aukerman and Sakai, 2003, Plant Cell, 15 (11), 2730-2741; Chen, 2003, Science, 303 (5666):2022-2025; Emery et al., 2003, Current Biology, 13 (20), 1768-1774; Palatnik et al., 2003, Nature, 425 (6955), 257-263). There is speculation that miRNAs may represent a new aspect of gene regulation.

Most miRNAs have been discovered by cloning. There are few cloning kits available for researchers from Ambion and QIAGEN etc. The process is laborious and less accurate. Further, there has been little reliable technology available for miRNA quantitation (Allawi et al., Third Wave Technologies, RNA. 2004 July; 10(7):1153-61). Northern blotting has been used but results are not quantitative (Lagos-Quitana et al., 2001, Science, 294 (5543), 853-854). Many miRNA researchers are interested in monitoring the level of the miRNAs at different tissues, at the different stages of development, or after treatment with various chemical agents. However, the short length of miRNAs has their study difficult.

SUMMARY

In some embodiments, the present teachings provide a method for detecting a micro RNA (miRNA) comprising; hybridizing the miRNA and a linker probe, wherein the linker probe comprises a stem, a loop, and a 3' target-specific portion, wherein the 3' target-specific portion base pairs with the 3' end region of the miRNA; extending the linker probe to form an extension reaction product; amplifying the extension reaction product to form an amplification product; and, detecting the miRNA.

In some embodiments, the present teachings provide a method for detecting a target polynucleotide comprising; hybridizing the target polynucleotide and a linker probe, wherein the linker probe comprises a stem, a loop, and a 3' target-specific portion, wherein the 3' target-specific portion base pairs with the 3' end region of the target polynucleotide; extending the linker probe to form an extension reaction product; amplifying the extension reaction product to form an amplification product in the presence of a detector probe, wherein the detector probe comprises a nucleotide of the linker probe stem in the amplification product or a nucleotide of the linker probe stem complement in the amplification product; and, detecting the target polynucleotide.

In some embodiments, the present teachings provide a method for detecting a miRNA molecule comprising; hybridizing the miRNA molecule and a linker probe, wherein the linker probe comprises a stem, a loop, and a 3' target specific portion, wherein the 3' target-specific portion base pairs with the 3' end region of the target polynucleotide; extending the linker probe to form an extension reaction product; amplifying the extension reaction product in the presence of a detector probe to form an amplification product, wherein the detector probe comprises a nucleotide of the linker probe stem in the amplification product or a nucleotide of the linker probe stem complement in the amplification product, and the detector probe further comprises a nucleotide of the 3' end region of the miRNA in the amplification product or a nucleotide of the 3' end region of the miRNA complement in the amplification product; and, detecting the miRNA molecule.

In some embodiments, the present teachings provide a method for detecting two different miRNAs from a single hybridization reaction comprising; hybridizing a first miRNA and a first linker probe, and a second miRNA and a second linker probe, wherein the first linker probe and the second linker probe each comprise a loop, a stem, and a 3' target-specific portion, wherein the 3' target-specific portion of the first linker probe base pairs with the 3' end region of the first miRNA, and wherein the 3' target-specific portion of the second linker probe base pairs with the 3' end region of the second miRNA; extending the first linker probe and the second linker probe to form extension reaction products; dividing the extension reaction products into a first amplification reaction to form a first amplification reaction product, and a second amplification reaction to form a second amplification reaction product, wherein a primer in the first amplification reaction corresponds with the first miRNA and not the second miRNA, and a primer in the second amplification reaction corresponds with the second miRNA and not the first miRNA, wherein a first detector probe in the first amplification reaction differs from a second detector probe in the second amplification reaction, wherein the first detector probe comprises a nucleotide of the first linker probe stem of the amplification product or a nucleotide of the first linker probe stem complement in the first amplification product, wherein the second detector probe comprises a nucleotide of the second linker probe stem of the amplification product or a nucleotide of the second linker probe stem complement in the amplification product; and, detecting the two different miRNAs.

In some embodiments, the present teachings provide a method for detecting two different target polynucleotides from a single hybridization reaction comprising; hybridizing a first target polynucleotide and a first linker probe, and a second target polynucleotide and a second linker probe, wherein the first linker probe and the second linker probe each comprise a loop, a stem, and a 3' target-specific portion, wherein the 3' target-specific portion of the first linker probe base pairs with the 3' end region of the first target polynucleotide, and wherein the 3' target-specific portion of the second linker probe base pairs with the 3' end region of the second target polynucleotide; extending the first linker probe and the second linker probe to form extension reaction products; dividing the extension reaction products into a first amplification reaction to form a first amplification reaction product and a second amplification reaction to form a second amplification reaction product; and, detecting the two different miRNA molecules.

In some embodiments, the present teachings provide a method for detecting a miRNA molecule from a cell lysate comprising; hybridizing the miRNA molecule from the cell lysate with a linker probe, wherein the linker probe comprises a stem, a loop, and a 3' target specific portion, wherein the 3' target-specific portion base pairs with the 3' end region of the miRNA; extending the linker probe to form an extension reaction product; amplifying the extension reaction product to form an amplification product in the presence of a detector probe, wherein the detector probe comprises a nucleotide of the linker probe stem of the amplification product or a nucleotide of the linker probe stem complement in the amplification product, and the detector probe further comprises a nucleotide of the 3' end region of the miRNA in the amplification product or a nucleotide of the 3' end region of the miRNA complement in the amplification product; and, detecting the miRNA molecule.

A kit comprising; a reverse transcriptase and a linker probe, wherein the linker probe comprises a stem, a loop, and a 3' target-specific portion, wherein the 3' target-specific portion corresponds to a miRNA.

The present teachings contemplate method for detecting a miRNA molecule comprising a step of hybridizing, a step of extending, a step of amplifying, and a step of detecting.

These and other features of the present teachings are set forth herein.

BRIEF DESCRIPTION OF THE DRAWINGS

The skilled artisan will understand that the drawings, described below, are for illustration purposes only. The drawings are not intended to limit the scope of the present teachings in any way.

FIG. 2 depicts certain aspects of various compositions according to some embodiments of the present teachings.

DESCRIPTION OF EXEMPLARY EMBODIMENTS

Figure 1:
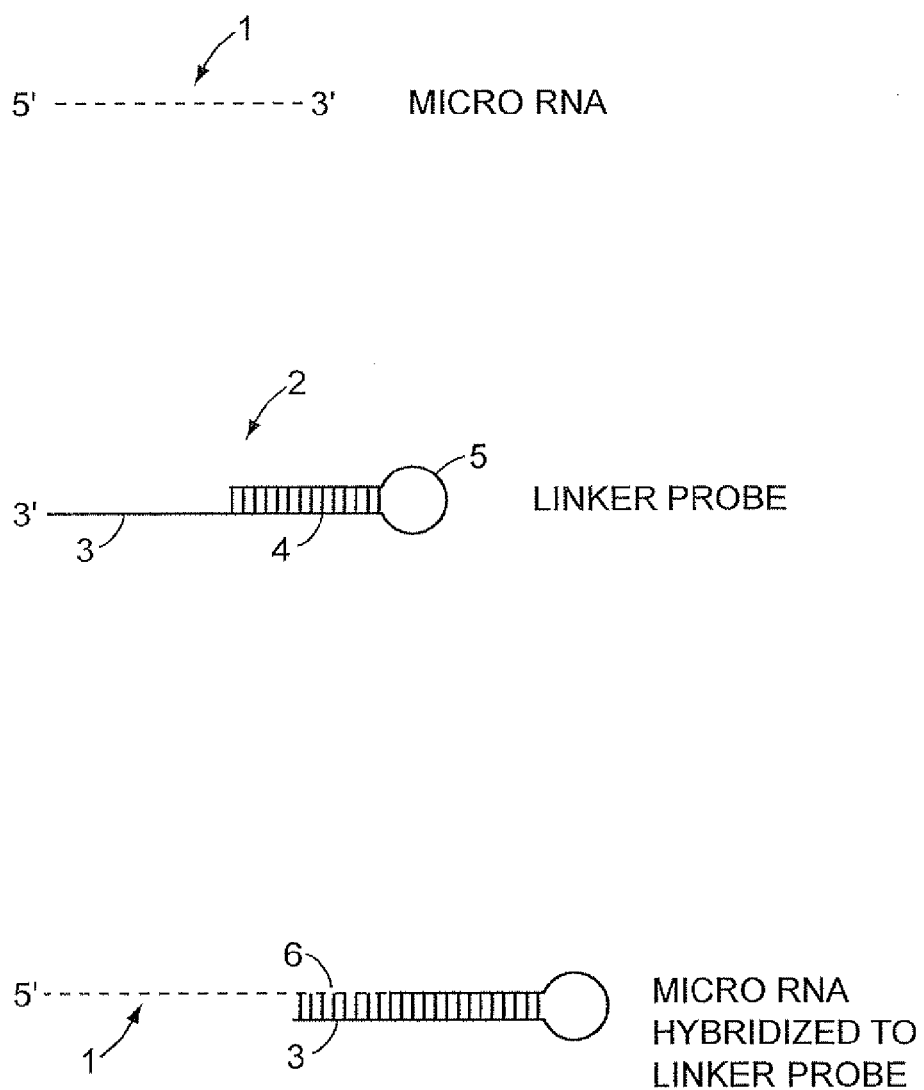
FIG. 1 depicts certain aspects of various compositions according to some embodiments of the present teachings.

Aspects of the present teachings may be further understood in light of the following examples, which should not be construed as limiting the scope of the present teachings in any way. The section headings used herein are for organizational purposes only and are not to be construed as limiting the described subject matter in any way. All literature and similar materials cited in this application, including but not limited to, patents, patent applications, articles, books, treatises, and internet web pages are expressly incorporated by reference in their entirety for any purpose. When definitions of terms in incorporated references appear to differ from the definitions provided in the present teachings, the definition provided in the present teachings shall control. It will be appreciated that there is an implied "about" prior to the temperatures, concentrations, times, etc discussed in the present teachings, such that slight and insubstantial deviations are within the scope of the present teachings herein. In this application, the use of the singular includes the plural unless specifically stated otherwise. For example, "a primer" means that more than one primer can, but need not, be present; for example but without limitation, one or more copies of a particular primer species, as well as one or more versions of a particular primer type, for example but not limited to, a multiplicity of different forward primers. Also, the use of "comprise", "comprises", "comprising", "contain", "contains", "containing", "include", "includes", and "including" are not intended to be limiting. It is to be understood that both the foregoing general description and the following detailed description are exemplary and explanatory only and are not restrictive of the invention.

Some Definitions

As used herein, the term "target polynucleotide" refers to a polynucleotide sequence that is sought to be detected. The target polynucleotide can be obtained from any source, and can comprise any number of different compositional components. For example, the target can be nucleic acid (e.g. DNA or RNA), transfer RNA, siRNA, and can comprise nucleic acid analogs or other nucleic acid mimic. The target can be methylated, non-methylated, or both. The target can be bisulfite-treated and non-methylated cytosines converted to uracil. Further, it will be appreciated that "target polynucleotide" can refer to the target polynucleotide itself, as well as surrogates thereof, for example amplification products, and native sequences. In some embodiments, the target polynucleotide is a miRNA molecule. In some embodiments, the target polynucleotide lacks a poly-A tail. In some embodiments, the target polynucleotide is a short DNA molecule derived from a degraded source, such as can be found in for example but not limited to forensics samples (see for example Butler, 2001, *Forensic DNA Typing: Biology and Technology Behind STR Markers*. The target polynucleotides of the present teachings can be derived from any of a number of sources, including without limitation, viruses, prokaryotes, eukaryotes, for example but not limited to plants, fungi, and animals. These sources may include, but are not limited to, whole blood, a tissue biopsy, lymph, bone marrow, amniotic fluid, hair, skin, semen, biowarfare agents, anal secretions, vaginal secretions, perspiration, saliva, buccal swabs, various environmental samples (for example, agricultural, water, and soil), research samples generally, purified samples generally, cultured cells, and lysed cells. It will be appreciated that target polynucleotides can be isolated from samples using any of a variety of procedures known in the art, for example the Applied Biosystems ABI Prism™ 6100 Nucleic Acid Prep-Station, and the ABI Prism™ 6700 Automated Nucleic Acid Workstation, Boom et al., U.S. Pat. No. 5,234,809., mirVana RNA isolation kit (Ambion), etc. It will be appreciated that target polynucleotides can be cut or sheared prior to analysis, including the use of such procedures as mechanical force, sonication, restriction endonuclease cleavage, or any method known in the art. In general, the target polynucleotides of the present teachings will be single stranded, though in some embodiments the target polynucleotide can be double stranded, and a single strand can result from denaturation.

As used herein, the term "3' end region of the target polynucleotide" refers to the region of the target to which the 3' target specific portion of the linker probe hybridizes. In some embodiments there can be a gap between the 3' end region of the target polynucleotide and the 5' end of the linker probe, with extension reactions filling in the gap, though generally such scenarios are not preferred because of the likely destabilizing effects on the duplex. In some embodiments, a miRNA molecule is the target, in which case the term "3' end region of the miRNA" is used.

As used herein, the term "linker probe" refers to a molecule comprising a 3' target specific portion, a stem, and a loop. Illustrative linker probes are depicted in FIG. 2 and elsewhere in the present teachings. It will be appreciated that the linker probes, as well as the primers of the present teachings, can be comprised of ribonucleotides, deoxynucleotides, modified ribonucleotides, modified deoxyribonucleotides, modified phosphate-sugar-backbone oligonucleotides, nucleotide analogs, or combinations thereof. For some illustrative teachings of various nucleotide analogs etc, see Fasman, 1989, Practical Handbook of Biochemistry and Molecular Biology, pp. 385-394, CRC Press, Boca Raton, Fla., Loakes, N.A.R. 2001, vol 29:2437-2447, and Pellestor et al., Int J Mol Med. 2004 April; 13(4):521-5.), references cited therein, and recent articles citing these reviews. It will be appreciated that the selection of the linker probes to query a given target polynucleotide sequence, and the selection of which collection of target polynucleotide sequences to query in a given reaction with which collection of linker probes, will involve procedures generally known in the art, and can involve the use of algorithms to select for those sequences with minimal secondary and tertiary structure, those targets with minimal sequence redundancy with other regions of the genome, those target regions with desirable thermodynamic characteristics, and other parameters desirable for the context at hand.

As used herein, the term "3' target-specific portion" refers to the single stranded portion of a linker probe that is complementary to a target polynucleotide. The 3' target-specific portion is located downstream from the stem of the linker probe. Generally, the 3' target-specific portion is between 6 and 8 nucleotides long. In some embodiments, the 3' target-specific portion is 7 nucleotides long. It will be appreciated that routine experimentation can produce other lengths, and that 3' target-specific portions that are longer than 8 nucleotides or shorter than 6 nucleotides are also contemplated by the present teachings. Generally, the 3'-most nucleotides of the 3' target-specific portion should have minimal complementarity overlap, or no overlap at all, with the 3' nucleotides of the forward primer; it will be appreciated that overlap in these regions can produce undesired primer dimer amplification products in subsequent amplification reactions. In some embodiments, the overlap between the 3'-most nucleotides of the 3' target-specific portion and the 3' nucleotides of the forward primer is 0, 1, 2, or 3 nucleotides. In some embodiments, greater than 3 nucleotides can be complementary between the 3'-most nucleotides of the 3' target-specific portion and the 3' nucleotides of the forward primer, but generally such scenarios will be accompanied by additional non-complementary nucleotides interspersed therein. In some embodiments, modified bases such as LNA can be used in the 3' target specific portion to increase the Tm of the linker probe (see for example Petersen et al., Trends in Biochemistry (2003), 21:2:74-81). In some embodiments, universal bases can be used, for example to allow for smaller libraries of linker probes. Universal bases can also be used in the 3' target specific portion to allow for the detection of unknown targets. For some descriptions of universal bases, see for example Loakes et al., Nucleic Acids Research, 2001, Volume 29, No. 12, 2437-2447. In some embodiments, modifications including but not limited to LNAs and universal bases can improve reverse transcription specificity and potentially enhance detection specificity.

As used herein, the term "stem" refers to the double stranded region of the linker probe that is between the 3' target-specific portion and the loop. Generally, the stem is between 6 and 20 nucleotides long (that is, 6-20 complementary pairs of nucleotides, for a total of 12-40 distinct nucleotides). In some embodiments, the stem is 8-14 nucleotides long. As a general matter, in those embodiments in which a portion of the detector probe is encoded in the stem, the stem can be longer. In those embodiments in which a portion of the detector probe is not encoded in the stem, the stem can be shorter. Those in the art will appreciate that stems shorter that 6 nucleotides and longer than 20 nucleotides can be identified in the course of routine methodology and without undue experimentation, and that such shorter and longer stems are contemplated by the present teachings. In some embodiments, the stem can comprise an identifying portion.

As used herein, the term "loop" refers to a region of the linker probe that is located between the two complementary strands of the stem, as depicted in FIG. 1 and elsewhere in the present teachings. Typically, the loop comprises single stranded nucleotides, though other moieties modified DNA or RNA, Carbon spacers such as C18, and/or PEG (polyethylene glycol) are also possible. Generally, the loop is between 4 and 20 nucleotides long. In some embodiments, the loop is between 14 and 18 nucleotides long. In some embodiments, the loop is 16 nucleotides long. As a general matter, in those embodiments in which a reverse primer is encoded in the loop, the loop can generally be longer. In those embodiments in which the reverse primer corresponds to both the target polynucleotide as well as the loop, the loop can generally be shorter. Those in the art will appreciate that loops shorter that 4 nucleotides and longer than 20 nucleotides can be identified in the course of routine methodology and without undue experimentation, and that such shorter and longer loops are contemplated by the present teachings. In some embodiments, the loop can comprise an identifying portion.

As used herein, the term "identifying portion" refers to a moiety or moieties that can be used to identify a particular linker probe species, and as a result determine a target polynucleotide sequence, and can refer to a variety of distinguishable moieties including zipcodes, a known number of nucleobases, and combinations thereof. In some embodiments, an identifying portion, or an identifying portion complement, can hybridize to a detector probe, thereby allowing detection of a target polynucleotide sequence in a decoding reaction. The terms "identifying portion complement" typically refers to at least one oligonucleotide that comprises at least one sequence of nucleobases that are at least substantially complementary to and hybridize with their corresponding identifying portion. In some embodiments, identifying portion complements serve as capture moieties for attaching at least one identifier portion: element complex to at least one substrate; serve as "pull-out" sequences for bulk separation procedures; or both as capture moieties and as pull-out sequences (see for example O'Neil, et al., U.S. Pat. Nos. 6,638,760, 6,514,699, 6,146,511, and 6,124,092). Typically, identifying portions and their corresponding identifying portion complements are selected to minimize: internal, self-hybridization; cross-hybridization with different identifying portion species, nucleotide sequences in a reaction composition, including but not limited to gDNA, different species of identifying portion complements, or target-specific portions of probes, and the like; but should be amenable to facile hybridization between the identifying portion and its corresponding identifying portion complement. Identifying portion sequences and identifying portion complement sequences can be selected by any suitable method, for example but not limited to, computer algorithms such as described in PCT Publication Nos. WO 96/12014 and WO 96/41011 and in European Publication No. EP 799,897; and the algorithm and parameters of SantaLucia (Proc. Natl. Acad. Sci. 95:1460-65 (1998)). Descriptions of identifying portions can be found in, among other places, U.S. Pat. No. 6,309,829 (referred to as "tag segment" therein); U.S. Pat. No. 6,451,525 (referred to as "tag segment" therein); U.S. Pat. No. 6,309,829 (referred to as "tag segment" therein); U.S. Pat. No. 5,981,176 (referred to as "grid oligonucleotides" therein); U.S. Pat. No. 5,935,793 (referred to as "identifier tags" therein); and PCT Publication No. WO 01/92579 (referred to as "addressable support-specific sequences" therein). In some embodiments, the stem of the linker probe, the loop of the linker probe, or combinations thereof can comprise an identifying portion, and the detector probe can hybridize to the corresponding identifying portion. In some embodiments, the detector probe can hybridize to both the identifying portion as well as sequence corresponding to the target polynucleotide. In some embodiments, at least two identifying portion: identifying portion complement duplexes have melting temperatures that fall within a $\Delta T_m$ range ($T_{max}$-$T_{min}$) of no more than 10° C. of each other. In some embodiments, at least two identifying portion: identifying portion complement duplexes have melting temperatures that fall within a $\Delta T_m$ range of 5° C. or less of each other. In some embodiments, at least two identifying portion: identifying portion complement duplexes have melting temperatures that fall within a $\Delta T_m$ range of 2° C. or less of each other.

In some embodiments, at least one identifying portion or at least one identifying portion complement is used to separate the element to which it is bound from at least one component of a ligation reaction composition, a digestion reaction composition, an amplified ligation reaction composition, or the like. In some embodiments, identifying portions are used to attach at least one ligation product, at least one ligation product surrogate, or combinations thereof, to at least one substrate. In some embodiments, at least one ligation product, at least one ligation product surrogate, or combinations thereof, comprise the same identifying portion. Examples of separation approaches include but are not limited to, separating a multiplicity of different element: identifying portion species using the same identifying portion complement, tethering a multiplicity of different element: identifying portion species to a substrate comprising the same identifying portion complement, or both. In some embodiments, at least one identifying portion complement comprises at least one label, at least one mobility modifier, at least one label binding portion, or combinations thereof. In some embodiments, at least one identifying portion complement is annealed to at least one corresponding identifying portion and, subsequently, at least part of that identifying portion complement is released and detected, see for example Published P.C.T. Application WO04/4634 to Rosenblum et al., and Published P.C.T. Application WO01/92579 to Wenz et al., As used herein, the term "extension reaction" refers to an elongation reaction in which the 3' target specific portion of a linker probe is extended to form an extension reaction product comprising a strand complementary to the target polynucleotide. In some embodiments, the target polynucleotide is a miRNA molecule and the extension reaction is a reverse transcription reaction comprising a reverse transcriptase. In some embodiments, the extension reaction is a reverse transcription reaction comprising a polymerase derived from a Eubacteria. In some embodiments, the extension reaction can comprise rTth polymerase, for example as commercially available from Applied Biosystems catalog number N808-0192, and N808-0098. In some embodiments, the target polynucleotide is a miRNA or other RNA molecule, and as such it will be appreciated that the use of polymerases that also comprise reverse transcription properties can allow for some embodiments of the present teachings to comprise a first reverse transcription reaction followed thereafter by an amplification reaction, thereby allowing for the consolidation of two reactions in essentially a single reaction. In some embodiments, the target polynucleotide is a short DNA molecule and the extension reaction comprises a polymerase and results in the synthesis of a $2^{nd}$ strand of DNA. In some embodiments, the consolidation of the extension reaction and a subsequent amplification reaction is further contemplated by the present teachings.

As used herein, the term "primer portion" refers to a region of a polynucleotide sequence that can serve directly, or by virtue of its complement, as the template upon which a primer can anneal for any of a variety of primer nucleotide extension reactions known in the art (for example, PCR). It will be appreciated by those of skill in the art that when two primer portions are present on a single polynucleotide, the orientation of the two primer portions is generally different. For example, one PCR primer can directly hybridize to a first primer portion, while the other PCR primer can hybridize to the complement of the second primer portion. In addition, "universal" primers and primer portions as used herein are generally chosen to be as unique as possible given the particular assays and host genomes to ensure specificity of the assay.

As used herein, the term "forward primer" refers to a primer that comprises an extension reaction product portion and a tail portion. The extension reaction product portion of the forward primer hybridizes to the extension reaction product. Generally, the extension reaction product portion of the forward primer is between 9 and 19 nucleotides in length. In some embodiments, the extension reaction product portion of the forward primer is 16 nucleotides. The tail portion is located upstream from the extension reaction product portion, and is not complementary with the extension reaction product; after a round of amplification however, the tail portion can hybridize to complementary sequence of amplification products. Generally, the tail portion of the forward primer is between 5-8 nucleotides long. In some embodiments, the tail portion of the forward primer is 6 nucleotides long. Those in the art will appreciate that forward primer tail portion lengths shorter than 5 nucleotides and longer than 8 nucleotides can be identified in the course of routine methodology and without undue experimentation, and that such shorter and longer forward primer tail portion lengths are contemplated by the present teachings. Further, those in the art will appreciate that lengths of the extension reaction product portion of the forward primer shorter than 9 nucleotides in length and longer than 19 nucleotides in length can be identified in the course of routine methodology and without undue experimentation, and that such shorter and longer extension reaction product portion of forward primers are contemplated by the present teachings.

As used herein, the term "reverse primer" refers to a primer that when extended forms a strand complementary to the target polynucleotide. In some embodiments, the reverse primer corresponds with a region of the loop of the linker probe. Following the extension reaction, the forward primer can be extended to form a second strand product. The reverse primer hybridizes with this second strand product, and can be extended to continue the amplification reaction. In some embodiments, the reverse primer corresponds with a region of the loop of the linker probe, a region of the stem of the linker probe, a region of the target polynucleotide, or combinations thereof. Generally, the reverse primer is between 13-16 nucleotides long. In some embodiments the reverse primer is 14 nucleotides long. In some embodiments, the reverse primer can further comprise a non-complementary tail region, though such a tail is not required. In some embodiments, the reverse primer is a "universal reverse primer," which indicates that the sequence of the reverse primer can be used in a plurality of different reactions querying different target polynucleotides, but that the reverse primer nonetheless is the same sequence.

The term "upstream" as used herein takes on its customary meaning in molecular biology, and refers to the location of a region of a polynucleotide that is on the 5' side of a "downstream" region. Correspondingly, the term "downstream" refers to the location of a region of a polynucleotide that is on the 3' side of an "upstream" region.

As used herein, the term "hybridization" refers to the complementary base-pairing interaction of one nucleic acid with another nucleic acid that results in formation of a duplex, triplex, or other higher-ordered structure, and is used herein interchangeably with "annealing." Typically, the primary interaction is base specific, e.g., A/T and G/C, by Watson/Crick and Hoogsteen-type hydrogen bonding. Base-stacking and hydrophobic interactions can also contribute to duplex stability. Conditions for hybridizing detector probes and primers to complementary and substantially complementary target sequences are well known, e.g., as described in Nucleic Acid Hybridization, A Practical Approach, B. Hames and S. Higgins, eds., IRL Press, Washington, D.C. (1985) and J. Wetmur and N. Davidson, Mol. Biol. 31:349 et seq. (1968). In general, whether such annealing takes place is influenced by, among other things, the length of the polynucleotides and the complementary, the pH, the temperature, the presence of mono- and divalent cations, the proportion of G and C nucleotides in the hybridizing region, the viscosity of the medium, and the presence of denaturants. Such variables influence the time required for hybridization. Thus, the preferred annealing conditions will depend upon the particular application. Such conditions, however, can be routinely determined by the person of ordinary skill in the art without undue experimentation. It will be appreciated that complementarity need not be perfect; there can be a small number of base pair mismatches that will minimally interfere with hybridization between the target sequence and the single stranded nucleic acids of the present teachings. However, if the number of base pair mismatches is so great that no hybridization can occur under minimally stringent conditions then the sequence is generally not a complementary target sequence. Thus, complementarity herein is meant that the probes or primers are sufficiently complementary to the target sequence to hybridize under the selected reaction conditions to achieve the ends of the present teachings.

As used herein, the term "amplifying" refers to any means by which at least a part of a target polynucleotide, target polynucleotide surrogate, or combinations thereof, is reproduced, typically in a template-dependent manner, including without limitation, a broad range of techniques for amplifying nucleic acid sequences, either linearly or exponentially. Exemplary means for performing an amplifying step include ligase chain reaction (LCR), ligase detection reaction (LDR), ligation followed by Q-replicase amplification, PCR, primer extension, strand displacement amplification (SDA), hyperbranched strand displacement amplification, multiple displacement amplification (MDA), nucleic acid strand-based amplification (NASBA), two-step multiplexed amplifications, rolling circle amplification (RCA) and the like, including multiplex versions or combinations thereof, for example but not limited to, OLA/PCR, PCR/OLA, LDR/PCR, PCR/PCR/LDR, PCR/LDR, LCR/PCR, PCR/LCR (also known as combined chain reaction—CCR), and the like. Descriptions of such techniques can be found in, among other places, Sambrook et al. Molecular Cloning, $3^{rd}$ Edition,; Ausbel et al.; PCR Primer: A Laboratory Manual, Diffenbach, Ed., Cold Spring Harbor Press (1995); The Electronic Protocol Book, Chang Bioscience (2002), Msuih et al., J. Clin. Micro. 34:501-07 (1996); The Nucleic Acid Protocols Handbook, R. Rapley, ed., Humana Press, Totowa, N.J. (2002); Abramson et al., Curr Opin Biotechnol. 1993 February; 4(1):41-7, U.S. Pat. No. 6,027,998; U.S. Pat. No. 6,605,451, Barany et al., PCT Publication No. WO 97/31256; Wenz et al., PCT Publication No. WO 01/92579; Day et al., Genomics, 29(1): 152-162 (1995), Ehrlich et al., Science 252:1643-50 (1991); Innis et al., PCR Protocols: A Guide to Methods and Applications, Academic Press (1990); Favis et al., Nature Biotechnology 18:561-64 (2000); and Rabenau et al., Infection 28:97-102 (2000); Belgrader, Barany, and Lubin, Development of a Multiplex Ligation Detection Reaction DNA Typing Assay, Sixth International Symposium on Human Identification, 1995 (available on the world wide web at: promega.com/geneticidproc/ussymp6proc/blegrad.html); LCR Kit Instruction Manual, Cat. #200520, Rev. #050002, Stratagene, 2002; Barany, Proc. Natl. Acad. Sci. USA 88:188-93 (1991); Bi and Sambrook, Nucl. Acids Res. 25:2924-2951 (1997); Zirvi et al., Nucl. Acid Res. 27:e40i-viii (1999); Dean et al., Proc Natl Acad Sci USA 99:5261-66 (2002); Barany and Gelfand, Gene 109:1-11 (1991); Walker et al., Nucl. Acid Res. 20:1691-96 (1992); Polstra et al., BMC Inf. Dis. 2:18-(2002); Lage et al., Genome Res. 2003 February; 13(2):294-307, and Landegren et al., Science 241:1077-80 (1988), Demidov, V., Expert Rev Mol Diagn. 2002 November; 2(6):542-8., Cook et al., J Microbiol Methods. 2003 May; 53(2):165-74, Schweitzer et al., Curr Opin Biotechnol. 2001 February; 12(1): 21-7, U.S. Pat. No. 5,830,711, U.S. Pat. No. 6,027,889, U.S. Pat. No. 5,686,243, Published P.C.T. Application WO0056927A3, and Published P.C.T. Application WO9803673A1. In some embodiments, newly-formed nucleic acid duplexes are not initially denatured, but are used in their double-stranded form in one or more subsequent steps. An extension reaction is an amplifying technique that comprises elongating a linker probe that is annealed to a template in the 5' to 3' direction using an amplifying means such as a polymerase and/or reverse transcriptase. According to some embodiments, with appropriate buffers, salts, pH, temperature, and nucleotide triphosphates, including analogs thereof, i.e., under appropriate conditions, a polymerase incorporates nucleotides complementary to the template strand starting at the 3'-end of an annealed linker probe, to generate a complementary strand. In some embodiments, the polymerase used for extension lacks or substantially lacks 5' exonuclease activity. In some embodiments of the present teachings, unconventional nucleotide bases can be introduced into the amplification reaction products and the products treated by enzymatic (e.g., glycosylases) and/or physical-chemical means in order to render the product incapable of acting as a template for subsequent amplifications. In some embodiments, uracil can be included as a nucleobase in the reaction mixture, thereby allowing for subsequent reactions to decontaminate carryover of previous uracil-containing products by the use of uracil-N-glycosylase (see for example Published P.C.T. Application WO9201814A2). In some embodiments of the present teachings, any of a variety of techniques can be employed prior to amplification in order to facilitate amplification success, as described for example in Radstrom et al., Mol Biotechnol. 2004 February; 26(2):133-46. In some embodiments, amplification can be achieved in a self-contained integrated approach comprising sample preparation and detection, as described for example in U.S. Pat. Nos. 6,153,425 and 6,649,378. Reversibly modified enzymes, for example but not limited to those described in U.S. Pat. No. 5,773,258, are also within the scope of the disclosed teachings. The present teachings also contemplate various uracil-based decontamination strategies, wherein for example uracil can be incorporated into an amplification reaction, and subsequent carry-over products removed with various glycosylase treatments (see for example U.S. Pat. No. 5,536,649, and U.S. Provisional Application 60/584,682 to Andersen et al.,). Those in the art will understand that any protein with the desired enzymatic activity can be used in the disclosed methods and kits. Descriptions of DNA polymerases, including reverse transcriptases, uracil N-glycosylase, and the like, can be found in, among other places, Twyman, Advanced Molecular Biology, BIOS Scientific Publishers, 1999; Enzyme Resource Guide, rev. 092298, Promega, 1998; Sambrook and Russell; Sambrook et al.; Lehninger; PCR: The Basics; and Ausbel et al.

As used herein, the term "detector probe" refers to a molecule used in an amplification reaction, typically for quantitative or real-time PCR analysis, as well as end-point analysis. Such detector probes can be used to monitor the amplification of the target polynucleotide. In some embodiments, detector probes present in an amplification reaction are suitable for monitoring the amount of amplicon(s) produced as a function of time. Such detector probes include, but are not limited to, the 5'-exonuclease assay (TaqMan® probes described herein (see also U.S. Pat. No. 5,538,848) various stem-loop molecular beacons (see e.g., U.S. Pat. Nos. 6,103, 476 and 5,925,517 and Tyagi and Kramer, 1996, Nature Biotechnology 14:303-308), stemless or linear beacons (see, e.g., WO 99/21881), PNA Molecular Beacons™ (see, e.g., U.S. Pat. Nos. 6,355,421 and 6,593,091), linear PNA beacons (see, e.g., Kubista et al., 2001, SPIE 4264:53-58), non-FRET probes (see, e.g., U.S. Pat. No. 6,150,097), Sunrise®/Amplifluor® probes (U.S. Pat. No. 6,548,250), stem-loop and duplex Scorpion™ probes (Solinas et al., 2001, Nucleic Acids Research 29:E96 and U.S. Pat. No. 6,589,743), bulge loop probes (U.S. Pat. No. 6,590,091), pseudo knot probes (U.S. Pat. No. 6,589,250), cyclicons (U.S. Pat. No. 6,383, 752), MGB Eclipse™ probe (Epoch Biosciences), hairpin probes (U.S. Pat. No. 6,596,490), peptide nucleic acid (PNA) light-up probes, self-assembled nanoparticle probes, and ferrocene-modified probes described, for example, in U.S. Pat. No. 6,485,901; Mhlanga et al., 2001, Methods 25:463-471; Whitcombe et al., 1999,. Nature Biotechnology. 17:804-807; Isacsson et al., 2000, Molecular Cell Probes. 14:321-328; Svanvik et al., 2000, Anal Biochem. 281:26-35; Wolffs et al., 2001, Biotechniques 766:769-771; Tsourkas et al., 2002, Nucleic Acids Research. 30:4208-4215; Riccelli et al., 2002, Nucleic Acids Research 30:4088-4093; Zhang et al., 2002 Shanghai. 34:329-332; Maxwell et al., 2002, J. Am. Chem. Soc. 124:9606-9612; Broude et al., 2002, Trends Biotechnol. 20:249-56; Huang et al., 2002, Chem Res. Toxicol. 15:118-126; and Yu et al., 2001, J. Am. Chem. Soc 14:11155-11161. Detector probes can also comprise quenchers, including without limitation black hole quenchers (Biosearch), Iowa Black (IDT), QSY quencher (Molecular Probes), and Dabsyl and Dabcel sulfonate/carboxylate Quenchers (Epoch). Detector probes can also comprise two probes, wherein for example a fluor is on one probe, and a quencher is on the other probe, wherein hybridization of the two probes together on a target quenches the signal, or wherein hybridization on the target alters the signal signature via a change in fluorescence. Detector probes can also comprise sulfonate derivatives of fluoresceinin dyes with SO3 instead of the carboxylate group, phosphoramidite forms of fluorescein, phosphoramidite forms of CY 5 (commercially available for example from Amersham). In some embodiments, interchelating labels are used such as ethidium bromide, SYBR® Green I (Molecular Probes), and PicoGreen® (Molecular Probes), thereby allowing visualization in real-time, or end point, of an amplification product in the absence of a detector probe. In some embodiments, real-time visualization can comprise both an intercalating detector probe and a sequence-based detector probe can be employed. In some embodiments, the detector probe is at least partially quenched when not hybridized to a complementary sequence in the amplification reaction, and is at least partially unquenched when hybridized to a complementary sequence in the amplification reaction. In some embodiments, the detector probes of the present teachings have a Tm of 63-69 C, though it will be appreciated that guided by the present teachings routine experimentation can result in detector probes with other Tms. In some embodiments, probes can further comprise various modifications such as a minor groove binder (see for example U.S. Pat. No. 6,486,308) to further provide desirable thermodynamic characteristics. In some embodiments, detector probes can correspond to identifying portions or identifying portion complements.

The term "corresponding" as used herein refers to a specific relationship between the elements to which the term refers. Some non-limiting examples of corresponding include: a linker probe can correspond with a target polynucleotide, and vice versa. A forward primer can correspond with a target polynucleotide, and vice versa. A linker probe can correspond with a forward primer for a given target polynucleotide, and vice versa. The 3' target-specific portion of the linker probe can correspond with the 3' region of a target polynucleotide, and vice versa. A detector probe can correspond with a particular region of a target polynucleotide and vice versa. A detector probe can correspond with a particular identifying portion and vice versa. In some cases, the corresponding elements can be complementary. In some cases, the corresponding elements are not complementary to each other, but one element can be complementary to the complement of another element.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AAB, BBC, AAABCCCC, CBBAAA, CABABB, and so forth. The skilled artisan will understand that typically there is no limit on the number of items or terms in any combination, unless otherwise apparent from the context.

As used herein, the term "reaction vessel" generally refers to any container in which a reaction can occur in accordance with the present teachings. In some embodiments, a reaction vessel can be an eppendorf tube, and other containers of the sort in common practice in modern molecular biology laboratories. In some embodiments, a reaction vessel can be a well in microtitre plate, a spot on a glass slide, or a well in an Applied Biosystems TaqMan Low Density Array for gene expression (formerly MicroCard™). For example, a plurality of reaction vessels can reside on the same support. In some embodiments, lab-on-a-chip like devices, available for example from Caliper and Fluidgm, can provide for reaction vessels. In some embodiments, various microfluidic approaches as described in U.S. Provisional Application 60/545,674 to Wenz et al., can be employed. It will be recognized that a variety of reaction vessel are available in the art and within the scope of the present teachings.

As used herein, the term "detection" refers to any of a variety of ways of determining the presence and/or quantity and/or identity of a target polynucleoteide. In some embodiments employing a donor moiety and signal moiety, one may use certain energy-transfer fluorescent dyes. Certain nonlimiting exemplary pairs of donors (donor moieties) and acceptors (signal moieties) are illustrated, e.g., in U.S. Pat. Nos. 5,863,727; 5,800,996; and 5,945,526. Use of some combinations of a donor and an acceptor have been called FRET (Fluorescent Resonance Energy Transfer). In some embodiments, fluorophores that can be used as signaling probes include, but are not limited to, rhodamine, cyanine 3 (Cy 3), cyanine 5 (Cy 5), fluorescein, Vic™, Liz™, Tamra™, 5-Fam™, 6-Fam™, and Texas Red (Molecular Probes). (Vic™, Liz™, Tamra™, 5-Fam™, and 6-Fam™ (all available from Applied Biosystems, Foster City, Calif.). In some embodiments, the amount of detector probe that gives a fluorescent signal in response to an excited light typically relates to the amount of nucleic acid produced in the amplification reaction. Thus, in some embodiments, the amount of fluorescent signal is related to the amount of product created in the amplification reaction. In such embodiments, one can therefore measure the amount of amplification product by measuring the intensity of the fluorescent signal from the fluorescent indicator. According to some embodiments, one can employ an internal standard to quantify the amplification product indicated by the fluorescent signal. See, e.g., U.S. Pat. No. 5,736,333. Devices have been developed that can perform a thermal cycling reaction with compositions containing a fluorescent indicator, emit a light beam of a specified wavelength, read the intensity of the fluorescent dye, and display the intensity of fluorescence after each cycle. Devices comprising a thermal cycler, light beam emitter, and a fluorescent signal detector, have been described, e.g., in U.S. Pat. Nos. 5,928,907; 6,015,674; and 6,174,670, and include, but are not limited to the ABI Prism® 7700 Sequence Detection System (Applied Biosystems, Foster City, Calif.), the ABI GeneAmp® 5700 Sequence Detection System (Applied Biosystems, Foster City, Calif.), the ABI GeneAmp® 7300 Sequence Detection System (Applied Biosystems, Foster City, Calif.), and the ABI GeneAmp® 7500 Sequence Detection System (Applied Biosystems). In some embodiments, each of these functions can be performed by separate devices. For example, if one employs a Q-beta replicase reaction for amplification, the reaction may not take place in a thermal cycler, but could include a light beam emitted at a specific wavelength, detection of the fluorescent signal, and calculation and display of the amount of amplification product. In some embodiments, combined thermal cycling and fluorescence detecting devices can be used for precise quantification of target nucleic acid sequences in samples. In some embodiments, fluorescent signals can be detected and displayed during and/or after one or more thermal cycles, thus permitting monitoring of amplification products as the reactions occur in "real time." In some embodiments, one can use the amount of amplification product and number of amplification cycles to calculate how much of the target nucleic acid sequence was in the sample prior to amplification. In some embodiments, one could simply monitor the amount of amplification product after a predetermined number of cycles sufficient to indicate the presence of the target nucleic acid sequence in the sample. One skilled in the art can easily determine, for any given sample type, primer sequence, and reaction condition, how many cycles are sufficient to determine the presence of a given target polynucleotide. As used herein, determining the presence of a target can comprise identifying it, as well as optionally quantifying it. In some embodiments, the amplification products can be scored as positive or negative as soon as a given number of cycles is complete. In some embodiments, the results may be transmitted electronically directly to a database and tabulated. Thus, in some embodiments, large numbers of samples can be processed and analyzed with less time and labor when such an instrument is used. In some embodiments, different detector probes may distinguish between different target polynucleoteides. A non-limiting example of such a probe is a 5'-nuclease fluorescent probe, such as a TaqMan® probe molecule, wherein a fluorescent molecule is attached to a fluorescence-quenching molecule through an oligonucleotide link element. In some embodiments, the oligonucleotide link element of the 5'-nuclease fluorescent probe binds to a specific sequence of an identifying portion or its complement. In some embodiments, different 5'-nuclease fluorescent probes, each fluorescing at different wavelengths, can distinguish between different amplification products within the same amplification reaction. For example, in some embodiments, one could use two different 5'-nuclease fluorescent probes that fluoresce at two different wavelengths ($WL_A$ and $WL_B$) and that are specific to two different stem regions of two different extension reaction products (A' and B', respectively). Amplification product A' is formed if target nucleic acid sequence A is in the sample, and amplification product B' is formed if target nucleic acid sequence B is in the sample. In some embodiments, amplification product A' and/or B' may form even if the appropriate target nucleic acid sequence is not in the sample, but such occurs to a measurably lesser extent than when the appropriate target nucleic acid sequence is in the sample. After amplification, one can determine which specific target nucleic acid sequences are present in the sample based on the wavelength of signal detected and their intensity. Thus, if an appropriate detectable signal value of only wavelength $WL_A$ is detected, one would know that the sample includes target nucleic acid sequence A, but not target nucleic acid sequence B. If an appropriate detectable signal value of both wavelengths $WL_A$ and $WL_B$ are detected, one would know that the sample includes both target nucleic acid sequence A and target nucleic acid sequence B. In some embodiments, detection can occur through any of a variety of mobility dependent analytical techniques based on differential rates of migration between different analyte species. Exemplary mobility-dependent analysis techniques include electrophoresis, chromatography, mass spectroscopy, sedimentation, e.g., gradient centrifugation, field-flow fractionation, multi-stage extraction techniques, and the like. In some embodiments, mobility probes can be hybridized to amplification products, and the identity of the target polynucleotide determined via a mobility dependent analysis technique of the eluted mobility probes, as described for example in Published P.C.T. Application WO04/46344 to Rosenblum et al., and WO01/92579 to Wenz et al.,. In some embodiments, detection can be achieved by various microarrays and related software such as the Applied Biosystems Array System with the Applied Biosystems 1700 Chemiluminescent Microarray Analyzer and other commercially available array systems available from Affymetrix, Agilent, Illumina, and Amersham Biosciences, among others (see also Gerry et al., J. Mol. Biol. 292:251-62, 1999; De Bellis et al., Minerva Biotec 14:247-52, 2002; and Stears et al., Nat. Med. 9:140-45, including supplements, 2003). It will also be appreciated that detection can comprise reporter groups that are incorporated into the reaction products, either as part of labeled primers or due to the incorporation of labeled dNTPs during an amplification, or attached to reaction products, for example but not limited to, via hybridization tag complements comprising reporter groups or via linker arms that are integral or attached to reacton products. Detection of unlabeled reaction products, for example using mass spectrometry, is also within the scope of the current teachings.

Exemplary Embodiments

FIG. 1 depicts certain compositions according to some embodiments of the present teachings. Top, a miRNA molecule (1, dashed line) is depicted. Middle, a linker probe (2) is depicted, illustrating a 3' target specific portion (3), a stem (4), and a loop (5). Bottom, a miRNA hybridized to a linker probe is depicted, illustrating the 3' target specific portion of the linker probe (3) hybridized to the 3' end region of the miRNA (6).

As shown in FIG. 2, a target polynucleotide (9, dotted line) is illustrated to show the relationship with various components of the linker probe (10), the detector probe (7), and the reverse primer (8), according to various non-limiting embodiments of the present teachings. For example as shown in FIG. 2A, in some embodiments the detector probe (7) can correspond with the 3' end region of the target polynucleotide in the amplification product as well as a region upstream from the 3' end region of the target polynucleotide in the amplification product. (Here, the detector probe is depicted as rectangle (7) with an F and a Q, symbolizing a TaqMan probe with a florophore (F) and a quencher (Q)). Also shown in FIG. 2A, the loop can correspond to the reverse primer (8). In some embodiments as shown in FIG. 2B, the detector probe (7) can correspond with a region of the amplification product corresponding with the 3' end region of the target polynucleotide in the amplification product, as well as a region upstream from the 3' end region of the target polynucleotide in the amplification product, as well as the linker probe stem in the amplification product. Also shown in FIG. 2B, the upstream region of the stem, as well as the loop, can correspond to the reverse primer (8). In some embodiments as shown in FIG. 2C, the detector probe can correspond to the amplification product in a manner similar to that shown in FIG. 2B, but the loop can correspond to the reverse primer (8). In some embodiments as shown in FIG. 2D, the detector probe (7) can correspond with the linker probe stem in the amplification product. Also shown in FIG. 2D, the upstream region of the stem, as well as the loop can correspond to the reverse primer (8). It will be appreciated that various related strategies for implementing the different functional regions of these compositions are possible in light of the present teachings, and that such derivations are routine to one having ordinary skill in the art without undue experimentation.

Figure 3:
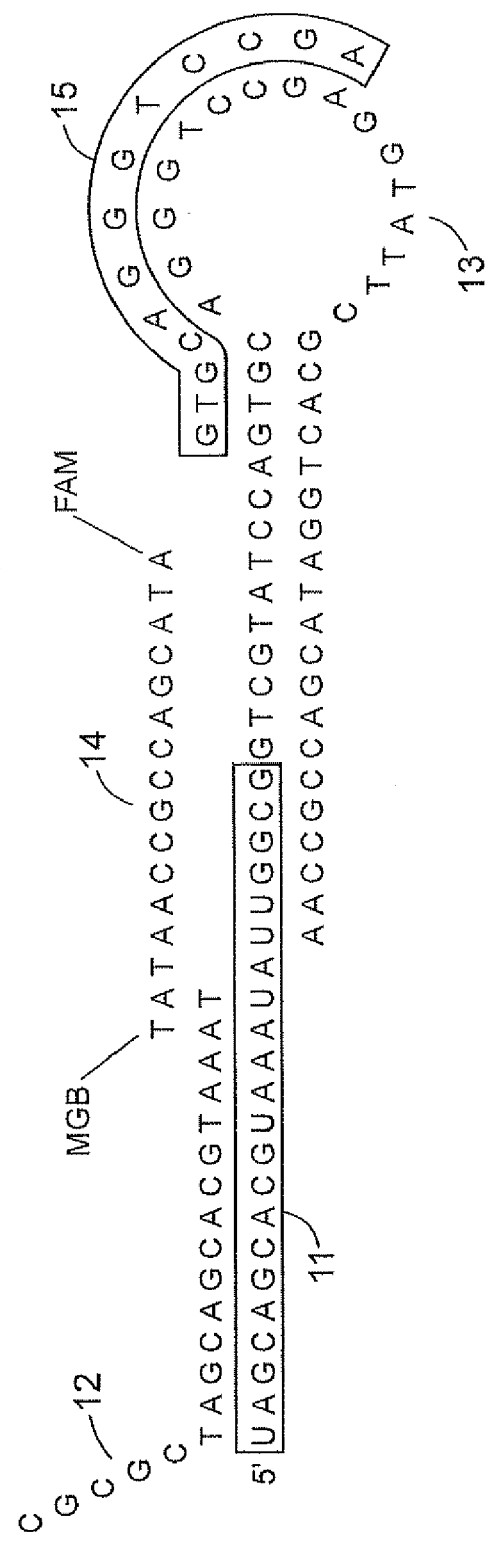
FIG. 3 depicts certain sequences of various compositions according to some embodiments of the present teachings.

FIG. 3 depicts the nucleotide relationship for the micro RNA MiR-16 (boxed, 11) according to some embodiments of the present teachings. Shown here is the interrelationship of MiR-16 to a forward primer (12), a linker probe (13), a TaqMan detector probe (14), and a reverse primer (boxed, 15). The TaqMan probe comprises a 3' minor groove binder (MGB), and a 5' FAM florophore. It will be appreciated that in some embodiments of the present teachings the detector probes, such as for example TaqMan probes, can hybridize to either strand of an amplification product. For example, in some embodiments the detector probe can hybridize to the strand of the amplification product corresponding to the first strand synthesized. In some embodiments, the detector probe can hybridize to the strand of the amplification product corresponding to the second strand synthesized.

Figure 4:
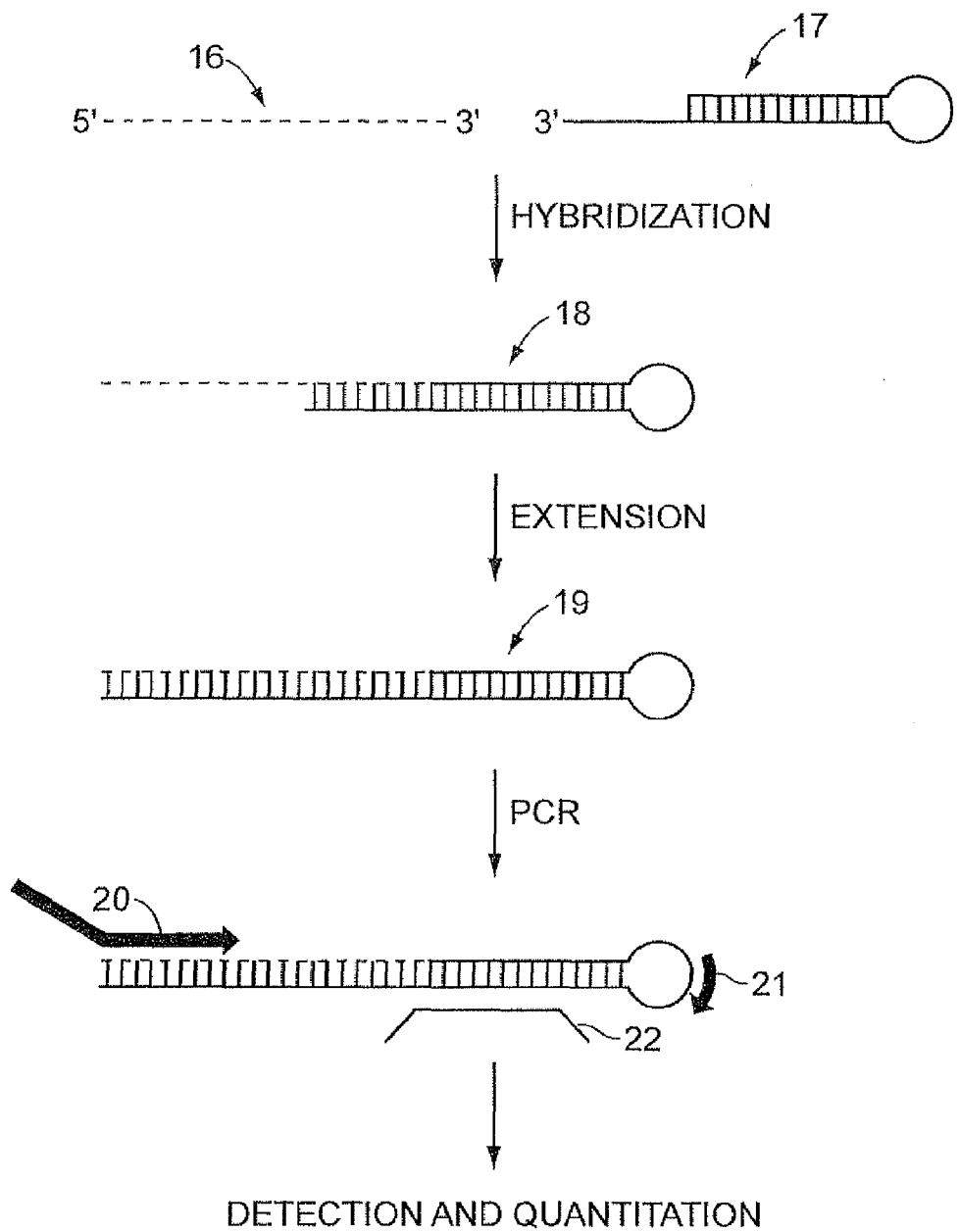
FIG. 4 depicts one single-plex assay design according to some embodiments of the present teachings.

FIG. 4 depicts a single-plex assay design according to some embodiments of the present teachings. Here, a miRNA molecule (16) and a linker probe (17) are hybridized together (18). The 3' end of the linker probe of the target-linker probe composition is extended to form an extension product (19) that can be amplified in a PCR. The PCR can comprise a miRNA specific forward primer (20) and a reverse primer (21). The detection of a detector probe (22) during the amplification allows for quantitation of the miRNA.

Figure 5:
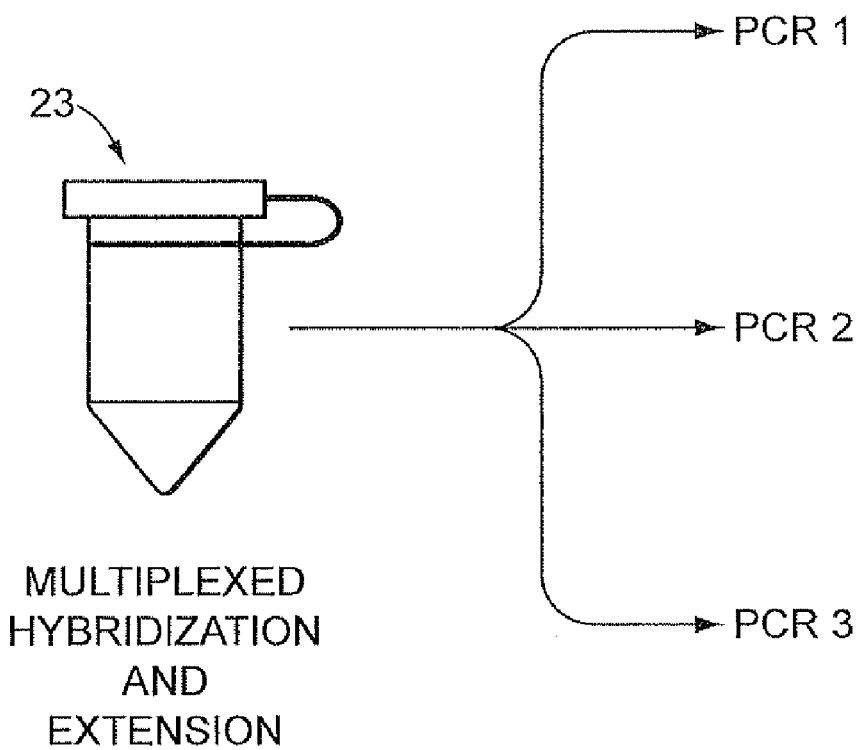
FIG. 5 depicts an overview of a multiplex assay design according to some embodiments of the present teachings.

FIG. 5 depicts an overview of a multiplex assay design according to some embodiments of the present teachings. Here, a multiplexed hybridization and extension reaction is performed in a first reaction vessel (23). Thereafter, aliquots of the extension reaction products from the first reaction vessel are transferred into a plurality of amplification reactions (here, depicted as PCRs 1, 2, and 3) in a plurality of second reaction vessels. Each PCR can comprise a distinct primer pair and a distinct detector probe. In some embodiments, a distinct primer pair but the same detector probe can be present in each of a plurality of PCRs.

Figure 6:
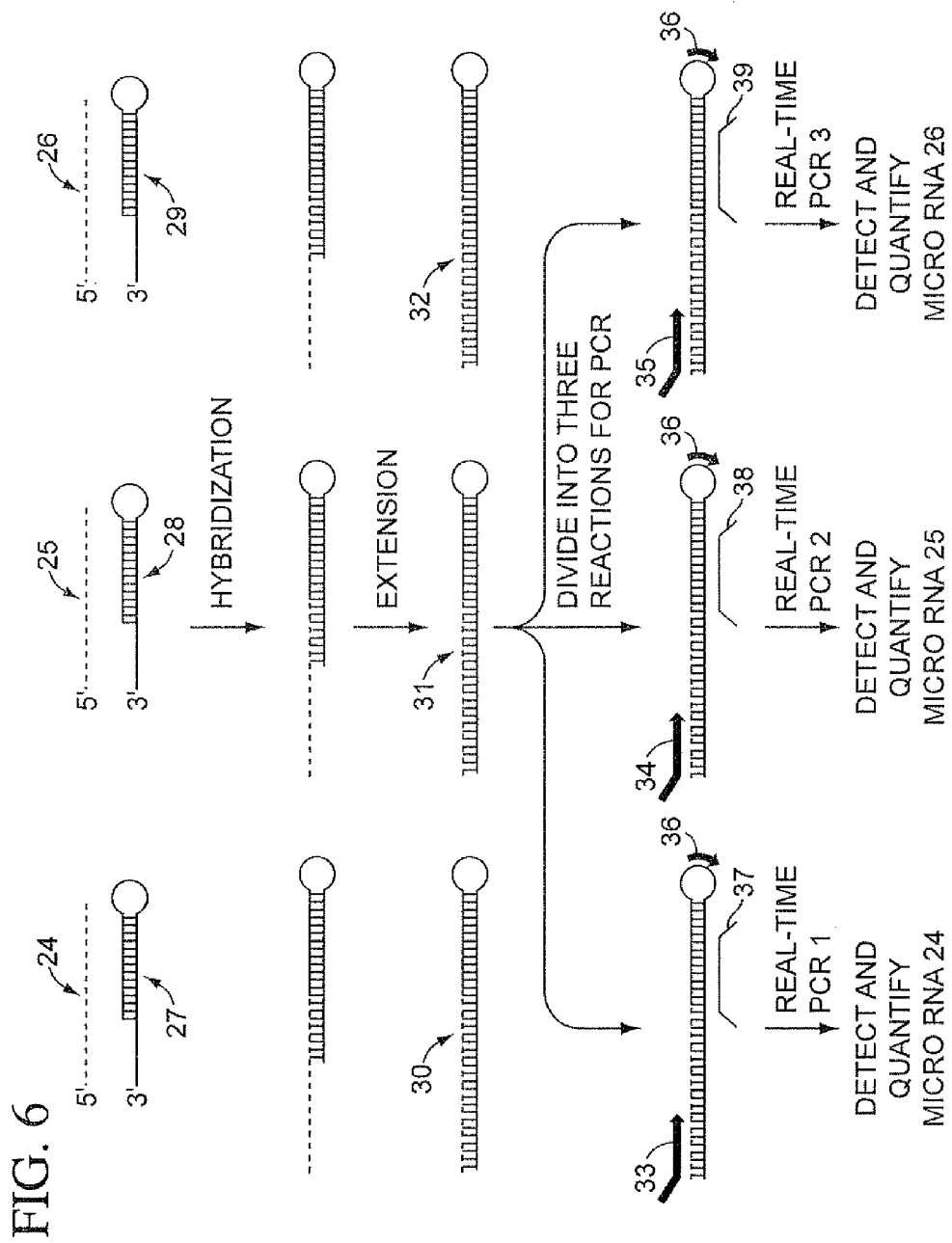
FIG. 6 depicts a multiplex assay design according to some embodiments of the present teachings.

FIG. 6 depicts a multiplex assay design according to some embodiments of the present teachings. Here, three different miRNAs (24, 25, and 26) are queried in a hybridization reaction comprising three different linker probes (27, 28, and 29). Following hybridization and extension to form extension products (30, 31, and 32), the extension products are divided into three separate amplification reactions. (Though not explicitly shown, it will be appreciated that a number of copies of the molecules depicted by 30, 31, and 32 can be present, such that each of the three amplification reactions can have copies of 30, 31, and 32.) PCR 1 comprises a forward primer specific for miRNA 24 (33), PCR 2 comprises a forward primer specific for miRNA 25 (34), and PCR 3 comprises a forward primer specific for miRNA 26 (35). Each of the forward primers further comprise a non-complementary tail portion. PCR 1, PCR 2, and PCR 3 all comprise the same universal reverse primer 36. Further, PCR 1 comprises a distinct detector probe (37) that corresponds to the 3' end region of miRNA 24 and the stem of linker probe 27, PCR 2 comprises a distinct detector probe (38) that corresponds to the 3' end region of miRNA 25 and the stem of linker probe 28, and PCR 3 comprises a distinct detector probe (39) that corresponds to the 3' region of miRNA 26 and the stem of linker probe 29.

The present teachings also contemplate reactions comprising configurations other than a linker probe. For example, in some embodiments, two hybridized molecules with a sticky end can be employed, wherein for example an overlapping 3' sticky end hybridizes with the 3' end region of the target polynucleotide. Some descriptions of two molecule configurations that can be employed in the present teachings can be found in Chen et al., U.S. Provisional Application 60/517, 470. Viewed in light of the present teachings herein, one of skill in the art will appreciate that the approaches of Chen et al., can also be employed to result in extension reaction products that are longer that the target polynucleotide. These longer products can be detected with detector probes by, for example, taking advantage of the additional nucleotides introduced into the reaction products.

The present teachings also contemplate embodiments wherein the linker probe is ligated to the target polynucleotide, as described for example in Chen et al., U.S. Provisional Application 60/575,661, and the corresponding co-filed U.S. Provisional application co-filed herewith Further, it will be appreciated that in some embodiments of the present teachings, the two molecule configurations in Chen et al., U.S. Provisional Application 60/517,470 can be applied in embodiments comprising the linker approaches discussed in Chen et al., U.S. Provisional Application 60/575, 661.

Generally however, the loop structure of the present teachings will enhance the Tm of the target polynucleotide-linker probe duplex. Without being limited to any particular theory, this enhanced Tm could possibly be due to base stacking effects. Also, the characteristics of the looped linker probe of the present teachings can minimize nonspecific priming during the extension reaction, and/or a subsequent amplification reaction such as PCR. Further, the looped linker probe of the present teachings can better differentiate mature and precursor forms of miRNA, as illustrated infra in Example 6.

The present teachings also contemplate encoding and decoding reaction schemes, wherein a first encoding extension reaction is followed by a second decoding amplification reaction, as described for example in Livak et al., U.S. Provisional Application 60/556,162, Chen et al., U.S. Provisional Application 60/556,157, Andersen et al., U.S. Provisional Application 60/556,224, and Lao et al., U.S. Provisional Application 60/556,163.

The present teachings also contemplate a variety of strategies to minimize the number of different molecules in multiplexed amplification strategies, as described for example in Whitcombe et al., U.S. Pat. No. 6,270,967.

In certain embodiments, the present teachings also provide kits designed to expedite performing certain methods. In some embodiments, kits serve to expedite the performance of the methods of interest by assembling two or more components used in carrying out the methods. In some embodiments, kits may contain components in pre-measured unit amounts to minimize the need for measurements by end-users. In some embodiments, kits may include instructions for performing one or more methods of the present teachings. In certain embodiments, the kit components are optimized to operate in conjunction with one another.

For example, the present teachings provide a kit comprising, a reverse transcriptase and a linker probe, wherein the linker probe comprises a stem, a loop, and a 3' target-specific portion, wherein the 3' target-specific portion corresponds to a miRNA. In some embodiments, the kits can comprise a DNA polymerase. In some embodiments, the kits can comprise a primer pair. In some embodiments, the kits can further comprise a forward primer specific for a miRNA, and, a universal reverse primer, wherein the universal reverse primer comprises a nucleotide of the loop of the linker probe. In some embodiments, the kits can comprise a plurality of primer pairs, wherein each primer pair is in one reaction vessel of a plurality of reaction vessels. In some embodiments, the kits can comprise a detector probe. In some embodiments, the detector probe comprises a nucleotide of the linker probe stem in the amplification product or a nucleotide of the linker probe stem complement in the amplification product, and the detector probe further comprises a nucleotide of the 3' end region of the miRNA in the amplification product or a nucleotide of the 3' end region of the miRNA complement in the amplification product.

The present teachings further contemplate kits comprising a means for hybridizing, a means for extending, a means for amplifying, a means for detecting, or combinations thereof.

While the present teachings have been described in terms of these exemplary embodiments, the skilled artisan will readily understand that numerous variations and modifications of these exemplary embodiments are possible without undue experimentation. All such variations and modifications are within the scope of the current teachings. Aspects of the present teachings may be further understood in light of the following examples, which should not be construed as limiting the scope of the teachings in any way.

EXAMPLE 1

A single-plex reaction was performed in replicate for a collection of mouse miRNAs, and the effect of the presence or absence of ligase, as well as the presence or absence of reverse transcriptase, determined. The results are shown in Table 1 as Ct values.

First, a 6 ul reaction was set up comprising: 1 ul Reverse Transcription Enzyme Mix (Applied Biosystems part number 4340444) (or 1 ul dH2O), 0.5 ul T4 DNA Ligase (400 units/ul, NEB) (or 0.5 ul dH20), 0.25 ul 2M KCl, 0.05 ul dNTPs (25 mM each), 0.25 ul T4 Kinase (10 units/ul, NEB), 1 ul 10×T4 DNA ligase buffer (NEB), 0.25 ul Applied Biosystems RNase Inhibitor (10 units/ul), and 2.2 ul dH20 Next, 2 ul of the linker probe (0.25 uM) and RNA samples (2 ul of 0.25 ug/ul mouse lung total RNA (Ambion, product number 7818) were added. Next, the reaction was mixed, spun briefly, and placed on ice for 5 minutes.

The reaction was then incubated at 16 C for 30 minutes, 42 C for 30 minutes, followed by 85 C for 5 minutes, and then held at 4 C. The reactions were diluted 4 times by adding 30 ul of dH20 prior to the PCR amplification.

A 10 ul PCR amplification was then set up comprising: 2 ul of diluted reverse transcription reaction product, 1.3 ul 10 uM miRNA specific Forward Primer, 0.7 ul 10 uM Universal Reverse Primer, 0.2 ul TaqMan detector probe, 0.2 ul dNTPs (25 mM each), 0.6 ul dH20, 5 ul 2× TaqMan master mix (Applied Biosystems, without UNG). The reaction was started with a 95 C step for 10 minutes. Then, 40 cycles were performed, each cycle comprising 95 C for 15 seconds, and 60 C for 1 minute. Table 1 indicates the results of this experiment.

TABLE 1

| Replicate | Ligase | Reverse transcriptase | Let-7a1 | mir16 | mir20 | mir21 | mir26a | mir30a | mir224 | miRNA average |
|---|---|---|---|---|---|---|---|---|---|---|
|   | Yes | Yes | 16.8 | 16.0 | 19.1 | 16.8 | 15.0 | 21.3 | 27.3 | 18.9 |
|   | Yes | No  | 38.7 | 31.3 | 39.9 | 31.9 | 30.1 | 33.3 | 40.0 | 35.0 |
| I | No  | Yes | 18.0 | 14.6 | 18.3 | 16.2 | 14.0 | 21.3 | 26.4 | 18.4 |
|   | No  | No  | 40.0 | 36.6 | 40.0 | 40.0 | 33.8 | 39.2 | 40.0 | 38.5 |
|   | Yes | Yes | 17.1 | 16.2 | 19.3 | 17.0 | 15.1 | 21.4 | 27.3 | 19.1 |
|   | Yes | No  | 38.9 | 31.2 | 37.6 | 32.1 | 30.4 | 33.4 | 39.4 | 34.7 |
| II | No | Yes | 18.4 | 14.8 | 18.7 | 16.6 | 14.3 | 21.5 | 26.7 | 18.7 |
|   | No  | No  | 40.0 | 36.1 | 40.0 | 40.0 | 34.1 | 40.0 | 40.0 | 38.6 |
| Replicate Average | Yes | Yes | 16.9 | 16.1 | 19.2 | 16.9 | 15.0 | 21.4 | 27.3 | 19.0 |
|   | Yes | No  | 38.8 | 31.2 | 38.8 | 32.0 | 30.3 | 33.4 | 39.7 | 34.9 |
|   | No  | Yes | 18.2 | 14.7 | 18.5 | 16.4 | 14.1 | 21.4 | 26.6 | 18.6 |
|   | No  | No  | 40.0 | 36.4 | 40.0 | 40.0 | 34.0 | 39.6 | 40.0 | 40.0 |

Sequences of corresponding forward primers, reverse primer, and TaqMan probes are shown in Table 2.

TABLE 2

| miRNA ID | miRNA sequences |
|---|---|
| miR-16 | uagcagcacguaaauauuggcg |
| miR-20 | uaaagugcuuauagugcaggua |
| miR-21 | uagcuuaucagacugauguuga |
| miR-22 | aagcugccaguugaagaacugu |
| miR-26a | uucaaguaauccaggauaggcu |
| miR-29 | cuagcaccaucugaaaucgguu |
| miR-30a | cuuucagucggauguuugcagc |
| miR-34 | uggcagugucuuagcugguugu |
| miR-200b | cucuaauacugccugguaaugaug |
| miR-323 | gcacauuacacggucgaccucu |
| miR-324-5 | cgcaucccuagggcauuggugu |
| let-7a1 | ugagguaguagguuguauaguu |

| Linker probe | Linker probe sequences |
|---|---|
| miR-16linR6 | GTCGTATCCAGTGCAGGGTCCGAGGTATTCGCACTGGATACGACCGCCAA |
| miR20LinR6 | GTCGTATCCAGTGCAGGGTCCGAGGTATTCGCACTGGATACGACTACCTG |
| miR-21linR6 | GTCGTATCCAGTGCAGGGTCCGAGGTATTCGCACTGGATACGACTCAACA |
| miR-22linR6 | GTCGTATCCAGTGCAGGGTCCGAGGTATTCGCACTGGATACGACACAGTT |
| miR-26alinR6 | GTCGTATCCAGTGCAGGGTCCGAGGTATTCGCACTGGATACGACAGCCTA |
| miR-29linR6 | GTCGTATCCAGTGCAGGGTCCGAGGTATTCGCACTGGATACGACAACCGA |
| miR30LinR6 | GTCGTATCCAGTGCAGGGTCCGAGGTATTCGCACTGGATACGACGCTGCA |
| miR-34linR6 | GTCGTATCCAGTGCAGGGTCCGAGGTATTCGCACTGGATACGACACAACC |
| miR-200blinR6 | GTCGTATCCAGTGCAGGGTCCGAGGTATTCGCACTGGATACGACCATCAT |
| miR-323linR6 | GTCGTATCCAGTGCAGGGTCCGAGGTATTCGCACTGGATACGACAGAGGT |

TABLE 2-continued

| | |
|---|---|
| miR-324-5linR6 | GTCGTATCCAGTGCAGGGTCCGAGGTATTCGCACTGGATACGACACACCA |
| let-7aLinR6 | GTCGTATCCAGTGCAGGGTCCGAGGTATTCGCACTGGATACGACAACTAT |
| Forward primer ID | Forward primer sequences |
| miR-16F55 | CGCGCTAGCAGCACGTAAAT |
| miR-20F56 | GCCGCTAAAGTGCTTATAGTGC |
| miR-21F56 | GCCCGCTAGCTTATCAGACTGATG |
| miR-22F56 | GCCTGAAGCTGCCAGTTGA |
| miR-26aF54 | CCGGCGTTCAAGTAATCCAGGA |
| miR-29F56 | GCCGCTAGCACCATCTGAAA |
| miR-30aF58 | GCCCCTTTCAGTCGGATGTTT |
| miR-34F56 | GCCCGTGGCAGTGTCTTAG |
| miR-200bF56 | GCCCCTCTAATACTGCCTGG |
| miR-323F58 | GCCACGCACATTACACGGTC |
| miR-324-5F56 | GCCACCATCCCCTAGGGC |
| let-7a1F56 | GCCGCTGAGGTAGTAGGTTGT |
| TaqMan probe ID | TaqMan probe sequences |
| miR-16_Tq8F67 | (6FAM)ATACGACCGCCAATAT(MGB) |
| miR20_Tq8F68 | (6FAM)CTGGATACGACTACCTG(MGB) |
| miR-21_Tq8F68 | (6FAM)CTGGATACGACTCAACA(MGB) |
| miR-22_Tq8F68 | (6FAM)TGGATACGACACAGTTCT(MGB) |
| miR-26a_Tq8F69 | (6FAM)TGGATACGACAGCCTATC(MGB) |
| miR-29_Tq8F68 | (6FAM)TGGATACGACAACCGAT(MGB) |
| miR30_Tq8F68 | (6FAM)CTGGATACGACGCTGC(MGB) |
| miR-34_Tq8F68 | (6FAM)ATACGACACAACCAGC(MGB) |
| miR-200b_Tq8F67 | (6FAM)ATACGACCATCATTACC(MGB) |
| miR-323_Tq8F67 | (6FAM)CTGGATACGACAGAGGT(MGB) |
| miR-324-5Tq8F68 | (6FAM)ATACGACACACCAATGC(MGB) |
| let7a_Tq8F68 | (6FAM)TGGATACGACAACTATAC(MGB) |
| Universal reverse primer ID | Reverse primer sequence |
| miR-UP-R67.8 | GTGCAGGGTCCGAGGT |

EXAMPLE 2

A multiplex (12-plex) assay was performed and the results compared to a corresponding collection of single-plex reactions. Additionally, the effect of the presence or absence of ligase, as well as the presence or absence of reverse transcriptase, was determined. The experiments were performed essentially the same as in Example 1, and the concentration of each linker in the 12-plex reaction was 0.05 uM, thereby resulting in a total linker probe concentration of 0.6 uM. Further, the diluted 12-plex reverse transcription product was split into 12 different PCR amplification reactions, wherein a miRNA forward primer and a universal reverse primer and a detector probe where in each amplification reaction. The miRNA sequences, Forward primers, and TaqMan detector probes are included in Table 2. The results are shown in Table 3.

TABLE 3

Singleplex vs. Multiplex Assay With Or Without T4 DNA Ligase

| miRNA | 1-plex Ct Ligation + RT | 1-plex Ct RT only | 12-plex Ct Ligation + RT | 12-plex Ct RT only | Ligation + RT vs RT only | 1- vs. 12-plex |
|---|---|---|---|---|---|---|
| let-7a1 | 17.8 | 16.3 | 17.6 | 17.0 | 1.0 | −0.3 |
| mir-16 | 16.0 | 15.1 | 16.1 | 15.3 | 0.9 | −0.1 |
| mir-20 | 19.3 | 18.7 | 19.8 | 19.5 | 0.4 | −0.6 |
| mir-21 | 17.0 | 15.8 | 17.1 | 16.3 | 1.0 | −0.3 |
| mir-22 | 21.6 | 20.4 | 21.4 | 20.7 | 1.0 | −0.1 |
| mir-26a | 15.2 | 14.3 | 15.6 | 14.9 | 0.8 | −0.4 |
| mir-29 | 17.9 | 16.8 | 17.7 | 17.0 | 0.9 | 0.0 |
| mir-30a | 20.7 | 19.9 | 21.2 | 20.7 | 0.7 | −0.7 |
| mir-34 | 21.3 | 20.4 | 22.0 | 21.0 | 0.9 | −0.6 |
| mir-200b | 19.9 | 19.2 | 21.1 | 20.2 | 0.8 | −1.0 |
| mir-323 | 32.5 | 31.2 | 33.6 | 32.3 | 1.3 | −1.1 |
| mir-324-5 | 24.7 | 23.1 | 25.0 | 24.4 | 1.1 | −0.8 |
| Average | 20.3 | 19.3 | 20.7 | 19.9 | 0.9 | −0.5 |

EXAMPLE 3

An experiment was performed to determine the effect of buffer conditions on reaction performance. In one set of experiments, a commercially available reverse transcription buffer from Applied Biosystems (part number 43400550) was employed in the hybridization and extension reaction. In a corresponding set of experiments, a commercially available T4 DNA ligase buffer (NEB) was employed in the hybridization and extension reaction. The experiments were performed as single-plex format essentially as described for Example 1, and each miRNA was done in triplicate. The results are shown in Table 4, comparing RT buffer (AB part #4340550) vs T4 DNA ligase buffer.

TABLE 4

| | RT Buffer | | | | T4 DNA Ligase Buffer | | | | RT vs |
|---|---|---|---|---|---|---|---|---|---|
| | I | II | III | Mean | I | II | III | Mean | T4 Buffer |
| let-7a1 | 22.7 | 22.8 | 22.8 | 22.8 | 20.8 | 20.7 | 20.6 | 20.7 | 2.1 |
| mir-16 | 18.4 | 18.5 | 18.6 | 18.5 | 17.7 | 17.8 | 17.9 | 17.8 | 0.7 |
| mir-20 | 23.6 | 23.7 | 23.8 | 23.7 | 23.1 | 23.1 | 23.0 | 23.1 | 0.6 |
| mir-21 | 20.4 | 20.4 | 20.5 | 20.4 | 19.4 | 19.3 | 19.2 | 19.3 | 1.1 |
| mir-22 | 24.0 | 23.9 | 24.1 | 24.0 | 22.7 | 22.7 | 22.7 | 22.7 | 1.3 |
| mir-26a | 19.8 | 19.9 | 20.1 | 19.9 | 18.9 | 19.0 | 19.0 | 18.9 | 1.0 |
| mir-29 | 21.3 | 21.3 | 21.4 | 21.3 | 20.5 | 20.6 | 20.5 | 20.5 | 0.8 |
| mir-30a | 24.4 | 24.4 | 24.4 | 24.4 | 23.6 | 23.4 | 23.6 | 23.5 | 0.9 |
| mir-34 | 24.9 | 24.8 | 25.1 | 25.0 | 23.0 | 23.1 | 23.2 | 23.1 | 1.9 |
| mir-200b | 25.8 | 25.8 | 25.9 | 25.9 | 24.6 | 24.6 | 24.8 | 24.7 | 1.2 |
| mir-323 | 34.6 | 34.5 | 34.8 | 34.6 | 34.7 | 34.2 | 34.5 | 34.5 | 0.2 |
| mir-324-5 | 26.0 | 26.0 | 26.1 | 26.0 | 25.4 | 25.7 | 25.6 | 25.6 | 0.5 |
| Average | 23.8 | 23.8 | 24.0 | 23.9 | 22.9 | 22.8 | 22.9 | 22.9 | 1.0 |

EXAMPLE 4

An experiment was performed to examine the effect of ligase and kinase in a real-time miRNA amplification reaction. Here, twelve single-plex reactions were performed in duplicate, essentially as described in Example 1. Results are shown in Table 5.

TABLE 5

| | Ligase & Kinase | | | No Ligase/No Kinase | | |
|---|---|---|---|---|---|---|
| | I | II | Mean | I | II | Mean |
| let-7a1 | 17.7 | 17.9 | 17.8 | 16.2 | 16.4 | 16.3 |
| mir-16 | 15.9 | 16.2 | 16.0 | 15.0 | 15.2 | 15.1 |
| mir-20 | 19.1 | 19.6 | 19.3 | 18.6 | 18.9 | 18.7 |
| mir-21 | 16.9 | 17.2 | 17.0 | 15.7 | 15.9 | 15.8 |
| mir-22 | 21.4 | 21.7 | 21.6 | 20.3 | 20.5 | 20.4 |
| mir-26a | 15.0 | 15.4 | 15.2 | 14.3 | 14.4 | 14.3 |
| mir-29 | 17.9 | 18.0 | 17.9 | 16.7 | 16.8 | 16.8 |
| mir-30a | 20.6 | 20.8 | 20.7 | 19.8 | 20.0 | 19.9 |
| mir-34 | 21.1 | 21.5 | 21.3 | 20.4 | 20.5 | 20.4 |
| mir-200b | 19.8 | 20.0 | 19.9 | 19.2 | 19.3 | 19.2 |
| mir-323 | 32.3 | 32.6 | 32.5 | 31.1 | 31.2 | 31.2 |
| mir-324-5 | 24.6 | 24.8 | 24.7 | 23.0 | 23.3 | 23.1 |
| Average | 20.2 | 20.5 | 20.3 | 19.2 | 19.4 | 19.3 |

EXAMPLE 5

An experiment was performed to determine the effect of sample material on Ct values in a real-time miRNA amplification reaction. Here, cells, GUHCl lysate, Tris lysate, and Purified RNA were compared. The cells were NIH3T3 cells. The Purified RNA was collected using the commercially available mirVana miRNA isolation kit for Ambion (catalog number 1560). A Tris lysate, and a Guanidine lysate (GuHCl) (commercially available from Applied Biosystems), were prepared as follows:

For the Tris lysate, a 1× lysis buffer comprised 10 mM Tris-HCl, pH 8.0, 0.02% Sodium Azide, and 0.03% Tween-20. Trypsinized cells were pelleted by centrifugation at 1500 rpm for 5 minutes. The growth media was removed by aspiration, being careful that the cell pellet was not disturbed.

PBS was added to bring the cells to 2×10³ cells/ul. Next 10 ul of cell suspension was mixed with 10 ul of a 2× lysis buffer and spun briefly. The tubes were then immediately incubated for 5 minutes at 95 C, and then immediately placed in a chilled block on ice for 2 minutes. The tubes were then mixed well and spun briefly at full speed before use (or optionally, stored at −20 C).

For the GuHCl lysate, a 1× lysis buffer comprised 2.5M GuHCl, 150 mM MES pH 6.0, 200 mM NaCl, 0.75% Tween-20. Trypsinized cells were pelleted by centrifugation at 1500 rpm for 5 minutes. The growth media was removed by aspiration, being careful that the cell pellet was not disturbed. The cell pellet was then re-suspended in 1×PBS, Ca++ and Mg++ free to bring cells to 2×10⁴ cells/uL. Then, 1 volume of 2× lysis buffer was added. To ensure complete nucleic acid release, this was followed by pipetting up and down ten times, followed by a brief spin. Results are shown in Table 6.

Similar results were obtained for a variety of cell lines, including NIH/3T3, OP9, A549, and HepG2 cells.

TABLE 6

| miRNA ID | Cells | GuHCl lysate | Tris lysate | Purified RNA |
|---|---|---|---|---|
| | | Ct | | |
| let-7a1 | 24.9 | 31.3 | 28.2 | 31.5 |
| mir-16 | 22.3 | 25.2 | 22.3 | 24.9 |
| mir-20 | 22.7 | 26.0 | 24.1 | 26.1 |
| mir-21 | 21.3 | 24.2 | 22.0 | 24.7 |
| mir-22 | 30.3 | 28.6 | 27.2 | 28.8 |
| mir-26a | 25.6 | 31.0 | 27.9 | 31.4 |
| mir-29 | 27.2 | 27.9 | 26.5 | 27.4 |
| mir-30a | 26.1 | 32.2 | 28.9 | 30.7 |
| mir-34 | 26.8 | 30.3 | 26.4 | 27.4 |
| mir-200b | 40.0 | 40.0 | 40.0 | 40.0 |
| mir-323 | 30.1 | 34.7 | 31.1 | 31.8 |
| mir-324-5 | 28.6 | 29.7 | 28.3 | 29.3 |
| Average | 27.2 | 30.1 | 27.8 | 29.5 |

EXAMPLE 6

An experiment was performed to demonstrate the ability of the reaction to selectively quantity mature miRNA in the presence of precursor miRNA. Here, let-7a miRNA and mir-26b miRNA were queried in both mature form as well as in their precursor form. Experiments were performed essentially as described for Example 1 in the no ligase condition, done in triplicate, with varying amounts of target material as indicated. Results are shown in Table 7. The sequences examined were as follows:

```
Mature let-7a, Seq ID NO:
UGAGGUAGUAGGUUGUAUAGUU

Precursor let-7a, SEQ ID NO: (Note that the
underlined sequences corresponds to the Mature
let-7a.)
GGGUGAGGUAGUAGGUUGUAUAGUUUGGGGCUCUGCCCUGCUAUGGGAUA

ACUAUACAAUCUACUGUCUUUCCU

Mature mir-26b, SEQ ID NO:
UUCAAGUAAUUCAGGAUAGGU

Precursor mir-26b of SEQ ID NO: (Note that the
underlined sequences corresponds to the Mature
mir-26b.)
CCGGGACCCAGUUCAAGUAAUUCAGGAUAGGUUGUGUGCUGUCCAGCCUG

UUCUCCAUUACUUGGCUCGGGGACCGG
```

TABLE 7

| Target | Mouse lung RNA (ng) | Synthetic miRNA (fM) | Synthetic precursor (fM) | Assay specific for (CT) miRNA | Precursor |
|---|---|---|---|---|---|
| Let-7a | 0 | 0 | 0 | 40.0 ± 0.0 | 40.0 ± 0.0 |
| (let-7a3) | 0 | 10 | 0 | 24.2 ± 0.3 | 40.0 ± 0.0 |
| | 0 | 100 | 0 | 21.0 ± 0.2 | 40.0 ± 0.0 |
| | 0 | 0 | 10 | 35.0 ± 1.0 | 25.0 ± 0.1 |
| | 0 | 0 | 100 | 31.0 ± 0.1 | 21.5 ± 0.1 |
| | 10 | 0 | 0 | 19.1 ± 0.4 | 40.0 ± 0.0 |
| Mir-26b | 0 | 0 | 0 | 40.0 ± 0.0 | 40.0 ± 0.0 |
| | 0 | 10 | 0 | 23.1 ± 0.1 | 40.0 ± 0.0 |
| | 0 | 100 | 0 | 19.7 ± 0.1 | 40.0 ± 0.0 |
| | 0 | 0 | 10 | 32.9 ± 0.4 | 25.7 ± 0.0 |
| | 0 | 0 | 100 | 28.9 ± 0.2 | 22.3 ± 0.0 |
| | 10 | 0 | 0 | 20.5 ± 0.1 | 28.0 ± 0.2 |

EXAMPLE 7

An experiment was performed on synthetic let-7a miRNA to assess the number of 3' nucleotides in the 3' target specific portion of the linker probe that correspond with the 3' end region of the miRNA. The experiment was performed as essentially as described supra for Example 1 for the no ligase condition, and results are shown in Table 8 as means and standard deviations of Ct values.

TABLE 8

| miRNA assay components: | let-7a |
| miRNA synthetic target: | let-7a |

| No. 3' ssDNA linker probe target specific portion bases | $C_T$ values & statistics | | | | |
|---|---|---|---|---|---|
| | I | II | III | Average | SD |
| 7 | 29.4 | 29.1 | 29.3 | 29.3 | 0.1 |
| 6 | 30.1 | 29.9 | 30.2 | 30.1 | 0.2 |
| 5 | 33.9 | 33.2 | 33.8 | 33.6 | 0.4 |
| 4 | 40.0 | 39.2 | 40.0 | 39.7 | 0.4 |

In some embodiments, 3' target specific portions of linker probes preferably comprise 5 nucleotides that correspond to the 3' end region of miRNAs. For example, miR-26a and miR-26b differ by only 2 bases, one of which is the 3' end nucleotide of miR-26a. Linker probes comprising 5 nucleotides at their 3' target specific portions can be employed to selectively detect miR-26a versus miR-26b.

Additional strategies for using the linker probes of the present teachings in the context of single step assays, as well as in the context of short primer compositions, can be found in filed U.S. Provisional Application "Compositions, Methods, and Kits for Identifying and Quantitating Small RNA Molecules" by Lao and Straus, as well as in Elfaitouri et al., J. Clin. Virol. 2004, 30(2): 150-156.

The present teachings further contemplate linker probe compositions comprising 3' target specific portions corresponding to any micro RNA sequence, including but without limitation, those sequences shown in Table 9, including *C. elegans* (cel), mouse (mmu), human (hsa), *drosophila* (dme), rat (rno), and rice (osa).

TABLE 9

| | |
|---|---|
| cel-let-7<br>ugagguaguagguuguauaguu | mmu-let-7<br>ugagguaguaguuuguacagu |
| cel-lin-4<br>ucccuaaccucaauua | mmu-let-7i<br>ugagguaguaguuugugcu |
| cel-miR-1<br>uggaauguaaagaaguaugua | mmu-miR-1<br>uggaauguaaagaaguaugua |
| cel-miR-2<br>uaucacagccagcuuugaugugc | mmu-miR-15b<br>uagcagcacaucaugguuuaca |
| cel-miR-34<br>aggcagugugguuagcugguug | mmu-miR-23b<br>aucacauugccagggauuaccac |
| cel-miR-35<br>ucaccggguggaaacuagcagu | mmu-miR-27b<br>uucacaguggcuaaguucug |
| cel-miR-36<br>ucaccgggugaaaauucgcaug | mmu-miR-29b<br>uagcaccauuugaaaucagugu |
| cel-miR-37<br>ucaccgggugaacacuugcagu | mmu-miR-30a*<br>uguaaacauccucgacuggaagc |
| cel-miR-38<br>ucaccgggagaaaaacuggagu | mmu-miR-30a<br>cuuucagucggauguuugcagc |
| cel-miR-39<br>ucaccgggguguaaaucagcuug | mmu-miR-30b<br>uguaaacauccuacacucagc |
| cel-miR-40<br>ucaccgggguguacaucagcuaa | mmu-miR-99a<br>acccguagauccgaucuugu |
| cel-miR-41<br>ucaccgggugaaaaaucaccua | mmu-miR-99b<br>cacccguagaaccgaccuugcg |
| cel-miR-42<br>caccggguuaacaucuacag | mmu-miR-101<br>uacaguacugugauaacuga |
| cel-miR-43<br>uaucacaguuuacuugcugucgc | mmu-miR-124a<br>uuaaggcacgcggugaaugcca |
| cel-miR-44<br>ugacuagagacacauucagcu | mmu-miR-125a<br>ucccugagacccuuuaaccugug |
| cel-miR-45<br>ugacuagagacacauucagcu | mmu-miR-125b<br>ucccugagacccuaacuuguga |
| cel-miR-46<br>ugucauggagucgcucucuuca | mmu-miR-126*<br>cauuauuacuuuugguacgcg |
| cel-miR-47<br>ugucauggaggcgcucucuuca | mmu-miR-126<br>ucguaccgugaguaauaaugc |
| cel-miR-48<br>ugagguaggcucaguagaugcga | mmu-miR-127<br>ucggauccgucugagcuuggcu |
| cel-miR-49<br>aagcaccacgagaagcugcaga | mmu-miR-128a<br>ucacagugaaccggucucuuuu |
| cel-miR-50<br>ugauaugucgguauucuuggguu | mmu-miR-130a<br>cagugcaauguuaaagggc |
| cel-miR-51<br>uacccguagcuccuauccauguu | mmu-miR-9<br>ucuuugguuaucuagcuguauga |
| cel-miR-52<br>cacccguacauaguguuccgugcu | mmu-miR-9*<br>uaaagcuagauaaccgaaagu |
| cel-miR-53<br>cacccguacauuuguuuccgugcu | mmu-miR-132<br>uaacagucuacagccauggucg |

TABLE 9-continued

| | |
|---|---|
| cel-miR-54<br>uacccguaaucuucauaauccgag | mmu-miR-133a<br>uuggucccuucaaccagcugu |
| cel-miR-55<br>uacccguauaaguuucugcugag | mmu-miR-134<br>ugugacugguugaccagaggg |
| cel-miR-56*<br>uggcggauccauuugggcuugua | mmu-miR-135a<br>uauggcuuuuauuccuauguga |
| cel-miR-56<br>uacccguaauguuuccgcugag | mmu-miR-136<br>acuccauuuguuugaugaugga |
| cel-miR-57<br>uacccuguagaucgagcugugugu | mmu-miR-137<br>uauugcuuaagaauacgcguag |
| cel-miR-58<br>ugagaucguucaguacggcaau | mmu-miR-138<br>agcugguguugugaauc |
| cel-miR-59<br>ucgaaucguuuaucaggaugaug | mmu-miR-140<br>agugguuuuacccuaugguag |
| cel-miR-60<br>uauuaugcacauuucuaguuca | mmu-miR-141<br>aacacugucugguaaagaugg |
| cel-miR-61<br>ugacuagaaccguuacucaucuc | mmu-miR-142-5p<br>cauaaaguagaaagcacuac |
| cel-miR-62<br>ugauauguaaucuagcuuacag | mmu-miR-142-3p<br>uguaguguuuccuacuuuaugg |
| cel-miR-63<br>uaugacacugaagcgaguuggaaa | mmu-miR-144<br>uacaguauagaugauguacuag |
| cel-miR-64<br>uaugacacugaagcguuaccgaa | mmu-miR-145<br>guccaguuuucccaggaaucccuu |
| cel-miR-65<br>uaugacacugaagcguaaccgaa | mmu-miR-146<br>ugagaacugaauuccauggguu |
| cel-miR-66<br>caugacacugauuagggauguga | mmu-miR-149<br>ucuggcuccgugucuucacucc |
| cel-miR-67<br>ucaaccuccuagaaagaguaga | mmu-miR-150<br>ucucccaacccuuguaccagug |
| cel-miR-68<br>ucgaagacucaaaaguguaga | mmu-miR-151<br>cuagacugaggcuccuugagg |
| cel-miR-69<br>ucgaaaauuaaaaaguguaga | mmu-miR-152<br>ucagugcaugacagaacuugg |
| cel-miR-70<br>uaauacgucguuggguguuuccau | mmu-miR-153<br>uugcauagucacaaaaguga |
| cel-miR-71<br>ugaaagacauggguaguga | mmu-miR-154<br>uagguuauccguguugccuucg |
| cel-miR-72<br>aggcaagauguuggcauagc | mmu-miR-155<br>uuaaugcuaauugugauagggg |
| cel-miR-73<br>uggcaagauguaggcaguucagu | mmu-miR-10b<br>cccuguagaaccgaauuugugu |
| cel-miR-74<br>uggcaagaaauggcagucuaca | mmu-miR-129<br>cuuuuugcggucgggcuugcu |
| cel-miR-75<br>uuaaagcuaccaaccggcuuca | mmu-miR-181a<br>aacauucaacgcugucggugagu |
| cel-miR-76<br>uucguuguugaugaagccuuga | mmu-miR-182<br>uuuggcaaugguagaacucaca |
| cel-miR-77<br>uucaucaggccauagcugucca | mmu-miR-183<br>uauggcacugguagaauucacug |
| cel-miR-78<br>uggaggccugguuguuugugc | mmu-miR-184<br>uggacggagaacugauaagggu |

TABLE 9-continued

| | |
|---|---|
| cel-miR-79<br>auaaagcuagguuaccaaagcu | mmu-miR-185<br>uggagagaaaggcaguuc |
| cel-miR-227<br>agcuuucgacaugauucugaac | mmu-miR-186<br>caaagaauucuccuuuugggcuu |
| cel-miR-80<br>ugagaucauuaguugaaagccga | mmu-miR-187<br>ucgugucuuguguugcagccgg |
| cel-miR-81<br>ugagaucaucgugaaagcuagu | mmu-miR-188<br>caucccuugcaugguggagggu |
| cel-miR-82<br>ugagaucaucgugaaagccagu | mmu-miR-189<br>gugccuacugagcugauaucagu |
| cel-miR-83<br>uagcaccauauaaauucaguaa | mmu-miR-24<br>uggcucaguucagcaggaacag |
| cel-miR-84<br>ugagguaguauguaauauugua | mmu-miR-190<br>ugauauguuugauauauuaggu |
| cel-miR-85<br>uacaaaguauuugaaaagucgugc | mmu-miR-191<br>caacggaaucccaaaagcagcu |
| cel-miR-86<br>uaagugaaugcuuugccacaguc | mmu-miR-193<br>aacuggccuacaaagucccag |
| cel-miR-87<br>uaagugaaugcuuugccacaguc | mmu-miR-194<br>uguaacagcaacuccaugugga |
| cel-miR-90<br>ugauauguuguugaaugcccc | mmu-miR-195<br>uagcagcacagaaauauuggc |
| cel-miR-124<br>uaaggcacgcggugaaugcca | mmu-miR-199a<br>cccaguguucagacuaccuguuc |
| cel-miR-228<br>aauggcacugcaugaauucacgg | mmu-miR-199a*<br>uacaguagucugcacauugguu |
| cel-miR-229<br>aaugacacugguuaucuuuuccaucgu | mmu-miR-200b<br>uaauacugccugguaaugaugac |
| cel-miR-230<br>guauuaguugugcgaccaggaga | mmu-miR-201<br>uacucaguaaggcauuguucu |
| cel-miR-231<br>uaagcucgugaucaacaggcagaa | mmu-miR-202<br>agagguauagcgcaugggaaga |
| cel-miR-232<br>uaaaugcaucuuaacugcgguga | mmu-miR-203<br>ugaaauguuuaggaccacuag |
| cel-miR-233<br>uugagcaaugcgcaugugcggga | mmu-miR-204<br>uucccuuuucauccuaugccug |
| cel-miR-234<br>uuuauugcucgagaauacccuu | mmu-miR-205<br>uccuucauuccaccggagucug |
| cel-miR-235<br>uauugcacucuccccggccuga | mmu-miR-206<br>uggaauguaaggaagugugugg |
| cel-miR-236<br>uaauacugucagguaaugacgcu | mmu-miR-207<br>gcuucuccuggcucuccucccuc |
| cel-miR-237<br>ucccugagaauucucgaacagcuu | mmu-miR-122a<br>uggagugacaaugguguuugu |
| cel-miR-238<br>uuuguacuccgaugccauucaga | mmu-miR-143<br>ugagaugaagcacuguagcuca |
| cel-miR-239a<br>uuuguacuacacauagguacugg | mmu-miR-30e<br>uguaaacauccuugacugga |
| cel-miR-239b<br>uuguacuacacaaaaguacug | mmu-miR-290<br>cucaaacuauggggggcacuuuuu |
| cel-miR-240<br>uacuggcccccaaaucuucgcu | mmu-miR-291-5p<br>caucaaaguggaggcccucucu |

TABLE 9-continued

| | |
|---|---|
| cel-miR-241<br>ugagguaggugcgagaaauga | mmu-miR-291-3p<br>aaagugcuuccacuuugugugcc |
| cel-miR-242<br>uugcguaggccuuugcuucga | mmu-miR-292-5p<br>acucaaacuggggcucuuuug |
| cel-miR-243<br>cgguacgaucgcggcgggauauc | mmu-miR-292-3p<br>aagugccgccagguuuugagugu |
| cel-miR-244<br>ucuuugguuguacaaagugguaug | mmu-miR-293<br>agugccgcagaguuuguagugu |
| cel-miR-245<br>auuggucccuccaaguagcuc | mmu-miR-294<br>aaagugcuucccuuuugugugu |
| cel-miR-246<br>uuacauguuucgggagguaggagcu | mmu-miR-295<br>aaagugcuacuacuuuugagucu |
| cel-miR-247<br>ugacuagagccuauucucuucuu | mmu-miR-296<br>agggccccccucaauccugu |
| cel-miR-248<br>uacacgugcacggauaacgcuca | mmu-miR-297<br>auguaugugugcaugugcaug |
| cel-miR-249<br>ucacaggacuuuugagcguugc | mmu-miR-298<br>ggcagaggagggcuguucuucc |
| cel-miR-250<br>ucacagucaacuguuggcaugg | mmu-miR-299<br>ugguuuaccgucccacauacau |
| cel-miR-251<br>uuaaguaguggugccgcucuuauu | mmu-miR-300<br>uaugcaagggcaagcucucuuc |
| cel-miR-252<br>uaaguaguaguguguccgcagguaac | mmu-miR-301<br>cagugcaauaguauugucaaagc |
| cel-miR-253<br>cacaccucacuaacacugacc | mmu-miR-302<br>uaagugcuuccauguuuuggga |
| cel-miR-254<br>ugcaaaucuuucgcgacuguagg | mmu-miR-34c<br>aggcaguguaguuagcugauugc |
| cel-miR-256<br>uggaaugcauagaagacugua | mmu-miR-34b<br>uaggcaguguaauuagcugauug |
| cel-miR-257<br>gaguaucaggaguacccaguga | mmu-let-7d<br>agagguaguagguugcauagu |
| cel-miR-258<br>gguuuugagaggaauccuuuu | mmu-let-7d*<br>cuauacgaccugcugccuuucu |
| cel-miR-259<br>aaaucucauccuaaucuggua | mmu-miR-106a<br>caaagugcuaacagugcaggua |
| cel-miR-260<br>gugaugucgaacucuuguag | mmu-miR-106b<br>uaaagugcugacagugcagau |
| cel-miR-261<br>uagcuuuuaguuuucacg | mmu-miR-130b<br>cagugcaaugaugaaagggcau |
| cel-miR-262<br>guuucucgauguuuucugau | mmu-miR-19b<br>ugugcaaauccaugcaaaacuga |
| cel-miR-264<br>ggcggguggguuguuguuaug | mmu-miR-30c<br>uguaaacauccuacacucucagc |
| cel-miR-265<br>ugagggaggaagggugguau | mmu-miR-30d<br>uguaaacauccccgacuggaag |
| cel-miR-266<br>aggcaagacuuuggcaaagc | mmu-miR-148a<br>ucagugcacuacagaacuuugu |
| cel-miR-267<br>cccgugaagugucugcugca | mmu-miR-192<br>cugaccuaugaauugaca |
| cel-miR-268<br>ggcaagaauuagaagcaguuuggu | mmu-miR-196<br>uagguaguuucauguuguugg |

TABLE 9-continued

| | |
|---|---|
| cel-miR-269<br>ggcaagacucuggcaaaacu | mmu-miR-200a<br>uaacacugucugguaacgaugu |
| cel-miR-270<br>ggcaugauguagcaguggag | mmu-miR-208<br>auaagacgagcaaaaagcuugu |
| cel-miR-271<br>ucgccgggugggaaagcauu | mmu-let-7a<br>ugagguaguagguuguauaguu |
| cel-miR-272<br>uguaggcaugggguguuug | mmu-let-7b<br>ugagguaguagguugugugguu |
| cel-miR-273<br>ugcccguacugugucggcug | mmu-let-7c<br>ugagguaguagguuguaugguu |
| cel-miR-353<br>caauugccaugucuugguauu | mmu-let-7e<br>ugagguaggagguuguauagu |
| cel-miR-354<br>accuuguuuguugcugcuccu | mmu-let-7f<br>ugagguaguagauuguauaguu |
| cel-miR-355<br>uuuguuuuagccugagcuaug | mmu-miR-15a<br>uagcagcacauaaugguuugug |
| cel-miR-356<br>uugagcaacgcgaacaaauca | mmu-miR-16<br>uagcagcacguaaauauuggcg |
| cel-miR-357<br>uaaaugccagucguugcagga | mmu-miR-18<br>uaaggugcaucuagugcagaua |
| cel-miR-358<br>caauugguaucccugucaagg | mmu-miR-20<br>uaaagugcuuauagugcagguag |
| cel-miR-359<br>ucacuggucuuucucugacga | mmu-miR-21<br>uagcuuaucagacugauguuga |
| cel-miR-360<br>ugaccguaaucccguucacaa | mmu-miR-22<br>aagcugccaguugaagaacugu |
| cel-lsy-6<br>uuuuguaugagacgcauuucg | mmu-miR-23a<br>aucacauugccagggauuucc |
| cel-miR-392<br>uaucaucgaucacgugugauga | mmu-miR-26a<br>uucaaguaauccaggauaggcu |
| | mmu-miR-26b<br>uucaaguaauucaggauagguu |
| hsa-let-7a<br>ugagguaguagguuguauaguu | mmu-miR-29a<br>cuagcaccaucugaaaucgguu |
| hsa-let-7b<br>ugagguaguagguugugugguu | mmu-miR-29c<br>uagcaccauuugaaaucgguua |
| hsa-let-7c<br>ugagguaguagguuguaugguu | mmu-miR-27a<br>uucacaguggcuaaguuccgc |
| hsa-let-7d<br>agagguaguagguugcauagu | mmu-miR-31<br>aggcaagaugcuggcauagcug |
| hsa-let-7e<br>ugagguaggagguuguauagu | mmu-miR-92<br>uauugcacuugucccggccug |
| hsa-let-7f<br>ugagguaguagauuguauaguu | mmu-miR-93<br>caaagugcuguucgugcagguag |
| hsa-miR-15a<br>uagcagcacauaaugguuugug | mmu-miR-96<br>uuuggcacuagcacauuuuugcu |
| hsa-miR-16<br>uagcagcacguaaauauuggcg | mmu-miR-34a<br>uggcagugucuuagcggguuguu |
| hsa-miR-17-5p<br>caaagugcuuacagugcagguagu | mmu-miR-98<br>ugagguaguaaguuguauuguu |
| hsa-miR-17-3p<br>acugcagugaaggcacuugu | mmu-miR-103<br>agcagcauuguacagggcuauga |

TABLE 9-continued

| | |
|---|---|
| hsa-miR-18<br>uaaggugcaucuagugcagaua | mmu-miR-323<br>gcacauuacacggucgaccucu |
| hsa-miR-19a<br>ugugcaaaucuaugcaaaacuga | mmu-miR-324-5p<br>cgcaucccuagggcauuggugu |
| hsa-miR-19b<br>ugugcaaauccaugcaaaacuga | mmu-miR-324-3p<br>ccacugcccaggugcugcugg |
| hsa-miR-20<br>uaaagugcuuauagugcaggua | mmu-miR-325<br>ccuaguaggugcucaguaagugu |
| hsa-miR-21<br>uagcuuaucagacugauguuga | mmu-miR-326<br>ccucugggcccuuccuccagu |
| hsa-miR-22<br>aagcugccaguugaagaacugu | mmu-miR-328<br>cuggcccucucugcccuuccgu |
| hsa-miR-23a<br>aucacauugccagggauuucc | mmu-miR-329<br>aacacacccagcuaaccuuuuu |
| hsa-miR-189<br>gugccuacugagcugauaucagu | mmu-miR-330<br>gcaaagcacagggccugcagaga |
| hsa-miR-24<br>uggcucaguucagcaggaacag | mmu-miR-331<br>gccccugggccuauccuagaa |
| hsa-miR-25<br>cauugcacuugucucggucuga | mmu-miR-337<br>uucagcuccuauaugaugccuuu |
| hsa-miR-26a<br>uucaaguaauccaggauaggcu | mmu-miR-338<br>uccagcaucagugauuuuguuga |
| hsa-miR-26b<br>uucaaguaauucaggauaggu | mmu-miR-339<br>ucccuguccuccaggagcuca |
| hsa-miR-27a<br>uucacaguggcuaaguuccgcc | mmu-miR-340<br>uccgucucaguuacuuuauagcc |
| hsa-miR-28<br>aaggagcucacagucuauugag | mmu-miR-341<br>ucgaucggucggucggucagu |
| hsa-miR-29a<br>cuagcaccaucugaaaucgguu | mmu-miR-342<br>ucucacacagaaaucgcacccguc |
| hsa-miR-30a*<br>uguaaacauccucgacuggaagc | mmu-miR-344<br>ugaucuagccaaagccugacugu |
| hsa-miR-30a<br>cuuucagucggauguuugcagc | mmu-miR-345<br>ugcugaccccuaguccagugc |
| hsa-miR-31<br>ggcaagaugcuggcauagcug | mmu-miR-346<br>ugucugcccgagugccugccucu |
| hsa-miR-32<br>uauugcacauuacuaaguugc | mmu-miR-350<br>uucacaaagcccauacacuuuac |
| hsa-miR-33<br>gugcauuguaguugcauug | mmu-miR-135b<br>uauggcuuuucauuccuaugug |
| hsa-miR-92<br>uauugcacuugucccggccugu | mmu-miR-101b<br>uacaguacugugauagcugaag |
| hsa-miR-93<br>aaagugcuguucgugcagguag | mmu-miR-107<br>agcagcauuguacagggcuauca |
| hsa-miR-95<br>uucaacgg guauuuauugagca | mmu-miR-10a<br>uacccguagauccgaauuugug |
| hsa-miR-96<br>uuuggcacuagcacauuuugc | mmu-miR-17-5p<br>caaagugcuuacagugcagguagu |
| hsa-miR-98<br>ugagguaguaaguuguauuguu | mmu-miR-17-3p<br>acugcagugagggcacuugu |
| hsa-miR-99a<br>aacccguagauccgaucuugug | mmu-miR-19a<br>ugugcaaaucuaugcaaaacuga |

TABLE 9-continued

| | |
|---|---|
| hsa-miR-100<br>aacccguagauccgaacuugug | mmu-miR-25<br>cauugcacuugucucggucuga |
| hsa-miR-101<br>uacaguacugugauaacugaag | mmu-miR-28<br>aaggagcucacagucuauugag |
| hsa-miR-29b<br>uagcaccauuugaaaucagu | mmu-miR-32<br>uauugcacauuacuaaguugc |
| hsa-miR-103<br>agcagcauuguacagggcuauga | mmu-miR-100<br>aacccguagauccgaacuugug |
| hsa-miR-105<br>ucaaaugcucagacuccugu | mmu-miR-139<br>ucuacagugcacgugucu |
| hsa-miR-106a<br>aaaagugcuuacagugcagguagc | mmu-miR-200c<br>aauacugccggguaaugaugga |
| hsa-miR-107<br>agcagcauuguacagggcuauca | mmu-miR-210<br>cugugcgugugacagcggcug |
| hsa-miR-192<br>cugaccuaugaauugacagcc | mmu-miR-212<br>uaacagucuccagucacggcc |
| hsa-miR-196<br>uagguaguucauguuguugg | mmu-miR-213<br>accaucgaccguugauuguacc |
| hsa-miR-197<br>uucccaccuucuccacccagc | mmu-miR-214<br>acagcaggcacagacaggcag |
| hsa-miR-198<br>gguccagaggggagauagg | mmu-miR-216<br>uaaucucagcuggcaacugug |
| hsa-miR-199a<br>cccaguguucagacuaccuguuc | mmu-miR-218<br>uugugcuugaucuaaccaugu |
| hsa-miR-199a*<br>uacaguagucugcacauugguu | mmu-miR-219<br>ugauugccaaacgcaauucu |
| hsa-miR-208<br>auaagacgagcaaaagcuugu | mmu-miR-223<br>ugucaguuugucaaauacccc |
| hsa-miR-148a<br>ucagugcacuacagaacuuugu | mmu-miR-320<br>aaaagcuggguugagagggcgaa |
| hsa-miR-30c<br>uguaaacauccuacacucucagc | mmu-miR-321<br>uaagccagggauguggguuc |
| hsa-miR-30d<br>uguaaacaucccogacuggaag | mmu-miR-33<br>gugcauuguaguugcauug |
| hsa-miR-139<br>ucuacagugcacgugucu | mmu-miR-211<br>uucccuuugucauccuuugccu |
| hsa-miR-147<br>guguguggaaaugcuucugc | mmu-miR-221<br>agcuacauugucugcuggguuu |
| hsa-miR-7<br>uggaagacuagugauuuuguu | mmu-miR-222<br>agcuacaucuggcuacugggucu |
| hsa-miR-10a<br>uacccuguagauccgaauuugug | mmu-miR-224<br>uaagucacuaguguuccguuua |
| hsa-miR-10b<br>uacccuguagaaccgaauuugu | mmu-miR-199b<br>cccaguguuuagacuaccuguuc |
| hsa-miR-34a<br>uggcagugucuuagcugguugu | mmu-miR-181b<br>aacauucauugcugucgguggguu |
| hsa-miR-181a<br>aacauucaacgcugucggugagu | mmu-miR-181c<br>aacauucaaccugucggugagu |
| hsa-miR-181b<br>aacauucauugcugucgguggguu | mmu-miR-128b<br>ucacagugaaccggucucuuuc |
| hsa-miR-181c<br>aacauucaaccugucggugagu | mmu-miR-7<br>uggaagacuagugauuuuguu |

TABLE 9-continued hsa-miR-182
uuuggcaauggguagaacucaca hsa-miR-182*
ugguucuagacuugccaacua hsa-miR-183
uauggcacugguagaauucacug hsa-miR-187
ucgugucuuguguugcagccg hsa-miR-199b
cccaguguuuagacuaucuguuc hsa-miR-203
gugaaauguuuaggaccacuag hsa-miR-204
uucccuuugucauccuaugccu hsa-miR-205
uccuucauuccaccggagucug hsa-miR-210
cugugcgugugacagcggcug hsa-miR-211
uucccuuugucauccuucgccu hsa-miR-212
uaacagucuccagucacggcc hsa-miR-213
accaucgaccguugauuguacc hsa-miR-214
acagcaggcacagacaggcag hsa-miR-215
augaccuaugaauugacagac hsa-miR-216
uaaucucagcuggcaacugug hsa-miR-217
uacugcaucaggaacugauggau hsa-miR-218
uugugcuugaucuaaccaugu hsa-miR-219
ugauugccaaacgcaauucu hsa-miR-220
ccacaccguaucugacacuuu hsa-miR-221
agcuacauugucugcuggguuuc hsa-miR-222
agcuacaucuggcuacugggucuc hsa-miR-223
ugucaguuugucaaauacccc hsa-miR-224
caagucacuagugguuccguuua hsa-miR-200b
cucuaauacugccugguaaugaug hsa-let-7g
ugagguaguaguuuuguacagu mmu-miR-7b
uggaagacuugugauuuuguu mmu-miR-217
uacugcaucaggaacugacuggau mmu-miR-133b
uuggucccuucaaccagcua mmu-miR-215
augaccuaugauuugacagac dme-miR-1
uggaauguaaagaaguauggag dme-miR-2a
uaucacagccagcuuugaugagc dme-miR-2b
uaucacagccagcuuugaggagc dme-miR-3
ucacugggcaaagugugucuca dme-miR-4
auaaagcuagacaaccauuga dme-miR-5
aaaggaacgaucguugugauaug dme-miR-6
uaucacaguggcuguucuuuuu dme-miR-7
uggaagacuagugauuuuguugu dme-miR-8
uaauacugucagguaaagauguc dme-miR-9a
ucuuugguuaucuagcuguauga dme-miR-10
acccuguagauccgaauuugu dme-miR-11
caucacagucugaguucuugc dme-miR-12
ugaguauuacaucagguacuggu dme-miR-13a
uaucacagccauuuugaugagu dme-miR-13b
uaucacagccauuuugacgagu dme-miR-14
ucagucuuuucucucuccua dme-miR-263a
guuaauggcacuggaagaauucac dme-miR-184*
ccuuaucauucucucgccccg dme-miR-184
uggacggagaacugauaagggc dme-miR-274
uuuugugaccgacacuaacggguaau

TABLE 9-continued

| | |
|---|---|
| hsa-let-7i<br>ugagguaguaguuugugcu | dme-miR-275<br>ucagguaccugaaguagcgcgcg |
| hsa-miR-1<br>uggaauguaaagaaguaugua | dme-miR-92a<br>cauugcacuugucccggccuau |
| hsa-miR-15b<br>uagcagcacaucaugguuuaca | dme-miR-219<br>ugauuguccaaacgcaauucuug |
| hsa-miR-23b<br>aucacauugccagggauuaccac | dme-miR-276a*<br>cagcgagguauagaguuccuacg |
| hsa-miR-27b<br>uucacaguggcuaaguucug | dme-miR-276a<br>uaggaacuucauaccgugcucu |
| hsa-miR-30b<br>uguaaacauccuacacucagc | dme-miR-277<br>uaaaugcacuaucugguacgaca |
| hsa-miR-122a<br>uggagugugacaauggugurugu | dme-miR-278<br>ucggugggacuuucguccguuu |
| hsa-miR-124a<br>uuaaggcacgcggugaaugcca | dme-miR-133<br>uuggucccuucaaccagcugu |
| hsa-miR-125b<br>ucccugagacccuaacuuguga | dme-miR-279<br>ugacuagauccacacucauuaa |
| hsa-miR-128a<br>ucacagugaaccggucucuuuu | dme-miR-33<br>aggugcauuguagucgcauug |
| hsa-miR-130a<br>cagugcaauguuaaagggc | dme-miR-280<br>uguauuuacguugcauaugaaaugaua |
| hsa-miR-132<br>uaacagucuacagccauggucg | dme-miR-281-1*<br>aagagagcuguccgucgacagu |
| hsa-miR-133a<br>uuggucccuucaaccagcugu | dme-miR-281<br>ugucauggaauugcucucuuugu |
| hsa-miR-135a<br>uauggcuuuuuauuccuauguga | dme-miR-282<br>aaucuagccucuacuaggcuuugucugu |
| hsa-miR-137<br>uauugcuuaagaauacgcguag | dme-miR-283<br>uaaauaucagcugguaauucu |
| hsa-miR-138<br>agcuggguguugugaauc | dme-miR-284<br>ugaagucagcaacuugauuccagcaauug |
| hsa-miR-140<br>aggguuuuacccuaugguag | dme-miR-281-2*<br>aagagagcuauccgucgacagu |
| hsa-miR-141<br>aacacugucugguaaagaugg | dme-miR-34<br>uggcagugugguuagcugguug |
| hsa-miR-142-5p<br>cauaaaguagaaagcacuac | dme-miR-124<br>uaaggcacgcggugaaugccaag |
| hsa-miR-142-3p<br>uguaguguuccuacuuuaugga | dme-miR-79<br>uaaagcuagauuaccaaagcau |
| hsa-miR-143<br>ugagaugaagcacuguagcuca | dme-miR-276b*<br>cagcgagguauagaguuccuacg |
| hsa-miR-144<br>uacaguauagaugaugu acuag | dme-miR-276b<br>uaggaacuuaauaccgugcucu |
| hsa-miR-145<br>guccaguuucccaggaaucccuu | dme-miR-210<br>uugugcgugugacagcggcua |
| hsa-miR-152<br>ucagugcaugacagaacuugg | dme-miR-285<br>uagcaccauucgaaaucagugc |
| hsa-miR-153<br>uugcauagucacaaaaguga | dme-miR-100<br>aacccguaaauccgaacuugug |
| hsa-miR-191<br>caacggaaucccaaaagcagcu | dme-miR-92b<br>aauugcacuaguccocggccugc |

TABLE 9-continued

| | |
|---|---|
| hsa-miR-9<br>ucuuugguuaucuagcuguauga | dme-miR-286<br>ugacuagaccgaacacucgugcu |
| hsa-miR-9*<br>uaaagcuagauaaccgaaagu | dme-miR-287<br>uguguugaaaaucguuugcac |
| hsa-miR-125a<br>ucccugagacccuuuaaccugug | dme-miR-87<br>uugagcaaaauuucaggugug |
| hsa-miR-126*<br>cauuauuacuuuugguacgcg | dme-miR-263b<br>cuuggcacugggagaauucac |
| hsa-miR-126<br>ucguaccgugaguaauaaugc | dme-miR-288<br>uuucaugucgauuucauuucaug |
| hsa-miR-127<br>ucggauccgucugagcuuggcu | dme-miR-289<br>uaaauauuuaaguggagccugcgacu |
| hsa-miR-129<br>cuuuugcggucugggcuugc | dme-bantam<br>ugagaucauuuugaaagcugauu |
| hsa-miR-134<br>ugugacugguugaccagaggg | dme-miR-303<br>uuuagguuucacaggaaacuggu |
| hsa-miR-136<br>acuccauuuguuuugaugaugga | dme-miR-31b<br>uggcaagaugucggaauagcug |
| hsa-miR-146<br>ugagaacugaauuccauggguu | dme-miR-304<br>uaaucucaauuuguaaaugugag |
| hsa-miR-149<br>ucuggcuccgugucuucacucc | dme-miR-305<br>auuguacuucaucaggugcucug |
| hsa-miR-150<br>ucucccaacccuuguaccagug | dme-miR-9c<br>ucuuugguauucuagcuguaga |
| hsa-miR-154<br>uagguuauccguguugccuucg | dme-miR-306<br>ucagguacuuagugacucucaa |
| hsa-miR-184<br>uggacggagaacugauaagggu | dme-miR-306*<br>gggggucacucugugccugugc |
| hsa-miR-185<br>uggagagaaaggcaguuc | dme-miR-9b<br>ucuuuggugauuuuagcuguaug |
| hsa-miR-186<br>caaagaauucuccuuuugggcuu | dme-let-7<br>ugagguaguagguuguauagu |
| hsa-miR-188<br>caucccuugcauggugggagggu | dme-miR-125<br>ucccugagacccuaacuguga |
| hsa-miR-190<br>ugauauguuugauauauuaggu | dme-miR-307<br>ucacaaccuccuugagugag |
| hsa-miR-193<br>aacuggccuacaaagucccag | dme-miR-308<br>aaucacaggauuauacugugag |
| hsa-miR-194<br>uguaacagcaacuccauggga | dme-miR-31a<br>uggcaagaugucggcauagcuga |
| hsa-miR-195<br>uagcagcacagaaauauuggc | dme-miR-309<br>gcacuggguaaaguuuguccua |
| hsa-miR-206<br>uggaauguaaggaagugugugg | dme-miR-310<br>uauugcacacuucccggccuuu |
| hsa-miR-320<br>aaaagcuggguugagagggcgaa | dme-miR-311<br>uauugcacauucaccggccuga |
| hsa-miR-321<br>uaagccagggauugugggguuc | dme-miR-312<br>uauugcacuugagacggccuga |
| hsa-miR-200c<br>aauacugccggguaaugaugga | dme-miR-313<br>uauugcacuuuucacagcccga |
| hsa-miR-155<br>uuaaugcuaaucugauagggg | dme-miR-314<br>uauucgagccaauaaguucgg |

TABLE 9-continued

| | |
|---|---|
| hsa-miR-128b<br>ucacagugaaccggucucuuuc | dme-miR-315<br>uuuugauuguugcucagaaagc |
| hsa-miR-106b<br>uaaagugcugacagugcagau | dme-miR-316<br>ugucuuuuccgcuuacuggcg |
| hsa-miR-29c<br>uagcaccauuugaaaucgguua | dme-miR-317<br>ugaacacagcuggugguauccagu |
| hsa-miR-200a<br>uaacacugucugguaacgaugu | dme-miR-318<br>ucacugggcuuuguuuaucuca |
| hsa-miR-302<br>uaagugcuuccauguuuugguga | dme-miR-2c<br>uaucacagccagcuuugaugggc |
| hsa-miR-34b<br>aggcagugucauuagcugauug | dme-miR-iab-4-5p<br>acguauacugaauguauccuga |
| hsa-miR-34c<br>aggcaguguaguuagcugauug | dme-miR-iab-4-3p<br>cgguauaccuucaguauacguaac |
| hsa-miR-299<br>ugguuuaccgucccacauacau | |
| hsa-miR-301<br>cagugcaauaguauugucaaagc | rno-miR-322<br>aaacaugaagcgcugcaaca |
| hsa-miR-99b<br>cacccguagaaccgaccuugcg | rno-miR-323<br>gcacauuacacggucgaccucu |
| hsa-miR-296<br>agggccccccucaauccugu | rno-miR-301<br>cagugcaauaguauugucaaagcau |
| hsa-miR-130b<br>cagugcaaugaugaaagggcau | rno-miR-324-5p<br>cgcaucccuagggcauuggugu |
| hsa-miR-30e<br>uguaaacauccuugacugga | rno-miR-324-3p<br>ccacugccccaggugcugcugg |
| hsa-miR-340<br>uccgucucaguuacuuuauagcc | rno-miR-325<br>ccuaguaggugcucaguaagugu |
| hsa-miR-330<br>gcaaagcacacggccugcagaga | rno-miR-326<br>ccucugggcccuuccuccagu |
| hsa-miR-328<br>cuggcccucucugcccuuccgu | rno-let-7d<br>agagguaguagguugcauagu |
| hsa-miR-342<br>ucucacacagaaaucgcacccguc | rno-let-7d*<br>cuauacgaccugcugccuuucu |
| hsa-miR-337<br>uccagcuccuauaugaugccuuu | rno-miR-328<br>cuggcccucucugcccuuccgu |
| hsa-miR-323<br>gcacauuacacggucgaccucu | rno-miR-329<br>aacacacccagcuaaccuuuuu |
| hsa-miR-326<br>ccucugggcccuuccuccag | rno-miR-330<br>gcaaagcacagggccugcagaga |
| hsa-miR-151<br>acuagacugaagcuccuugagg | rno-miR-331<br>gccccugggccuauccuagaa |
| hsa-miR-135b<br>uauggcuuucauuccuaugug | rno-miR-333<br>guggugugcuaguuacuuuu |
| hsa-miR-148b<br>ucagugcaucacagaacuuugu | rno-miR-140<br>agugguuuacccuauggguag |
| hsa-miR-331<br>gccccugggccuauccuagaa | rno-miR-140*<br>uaccacaggguagaaccacggaca |
| hsa-miR-324-5p<br>cgcaucccuagggcauuggugu | rno-miR-336<br>ucacccuuccauaucuagucu |
| hsa-miR-324-3p<br>ccacugccccaggugcugcugg | rno-miR-337<br>uucagcuccuauaugaugccuuu |

TABLE 9-continued

| | |
|---|---|
| hsa-miR-338<br>uccagcaucagugauuuuguuga | rno-miR-148b<br>ucagugcaucacagaacuuugu |
| hsa-miR-339<br>ucccuguccuccaggagcuca | rno-miR-338<br>uccagcaucagugauuuuguuga |
| hsa-miR-335<br>ucaagagcaauaacgaaaaaugu | rno-miR-339<br>ucccuguccuccaggagcuca |
| hsa-miR-133b<br>uuggucccuucaaccagcua | rno-miR-341<br>ucgaucggucggucgucagu |
| | rno-miR-342<br>ucucacacagaaaucgcacccguc |
| osa-miR156<br>ugacagaagagagugagcac | rno-miR-344<br>ugaucuagccaaagccugaccgu |
| osa-miR160<br>ugccuggcucccuguaugcca | rno-miR-345<br>ugcugaccccuaguccagugc |
| osa-miR162<br>ucgauaaaccucugcauccag | rno-miR-346<br>ugucugccugagugccugccucu |
| osa-miR164<br>uggagaagcagggcacgugca | rno-miR-349<br>cagcccugcugucuuaaccucu |
| osa-miR166<br>ucggaccaggcuucauucccc | rno-miR-129<br>cuuuuugcggucugggcuugcu |
| osa-miR167<br>ugaagcugccagcaugaucua | rno-miR-129*<br>aagcccuuaccccaaaaagcau |
| osa-miR169<br>cagccaaggaugacuugccga | rno-miR-20<br>uaaagugcuuauagugcagguag |
| osa-miR171<br>ugauugagccgcgccaauauc | rno-miR-20*<br>acugcauuacgagcacuuaca |
| | rno-miR-350<br>uucacaaagcccauacacuuucac |
| | rno-miR-7<br>uggaagacuagugauuuuguu |
| | rno-miR-7*<br>caacaaaucacagucugccaua |
| | rno-miR-351<br>ucccugaggagcccuuugagccug |
| | rno-miR-135b<br>uauggcuuuucauuccuaugug |
| | rno-miR-151*<br>ucgaggagcucacagucuagua |
| | rno-miR-151<br>acuagacugaggcuccuugagg |
| | rno-miR-101b<br>uacaguacugugauagcugaag |
| | rno-let-7a<br>ugagguaguagguuguauaguu |
| | rno-let-7b<br>ugagguaguagguugugugguu |
| | rno-let-7c<br>ugagguaguagguuguaugguu |
| | rno-let-7e<br>ugagguaggagguuguauagu |
| | rno-let-7f<br>ugagguaguagauuguauaguu |

TABLE 9-continued

```
rno-let-7i
ugagguaguaguuugugcu rno-miR-7b
uggaagacuugugauuuuguu rno-miR-9
ucuuugguuaucuagcuguauga rno-miR-10a
uacccuguagauccgaauuugug rno-miR-10b
uacccuguagaaccgaauuugu rno-miR-15b
uagcagcacaucaugguuuaca rno-miR-16
uagcagcacguaaauauuggcg rno-miR-17
caaagugcuuacagugcagguagu rno-miR-18
uaaggugcaucuagugcagaua rno-miR-19b
ugugcaauccaugcaaaacuga rno-miR-19a
ugugcaaaucaugcaaaacuga rno-miR-21
uagcuuaucagacugauguuga rno-miR-22
aagcugccaguugaagaacugu rno-miR-23a
aucacauugccagggauuucc rno-miR-23b
aucacauugccagggauuaccac rno-miR-24
uggcucaguucagcaggaacag rno-miR-25
cauugcacuugucucggucuga rno-miR-26a
uucaaguaauccaggauaggcu rno-miR-26b
uucaaguaauucaggauagguu rno-miR-27b
uucacaguggcuaaguucug rno-miR-27a
uucacaguggcuaaguuccgc rno-miR-28
aaggagcucacagucuauugag rno-miR-29b
uagcaccauuugaaaucagugu rno-miR-29a
cuagcaccaucugaaaucgguu rno-miR-29c
uagcaccauuugaaaucgguua rno-miR-30c
uguaaacauccuacacucucagc
```

TABLE 9-continued rno-miR-30e
uguaaacauccuugacugga rno-miR-30b
uguaaacauccuacacucagc rno-miR-30d
uguaaacauccccgacuggaag rno-miR-30a
cuuucagucggauguuugcagc rno-miR-31
aggcaagaugcuggcauagcug rno-miR-32
uauugcacauuacuaaguugc rno-miR-33
gugcauuguaguugcauug rno-miR-34b
uaggcaguguaauuagcugauug rno-miR-34c
aggcaguguaguuagcugauugc rno-miR-34a
uggcagugucuuagcugguuguu rno-miR-92
uauugcacuugucccggccug rno-miR-93
caaagugcuguucgugcagguag rno-miR-96
uuuggcacuagcacauuuuugcu rno-miR-98
ugagguaguaaguuguauuguu rno-miR-99a
aacccguagauccgaucuugug rno-miR-99b
cacccguagaaccgaccuugcg rno-miR-100
aacccguagauccgaacuugug rno-miR-101
uacaguacugugauaacugaag rno-miR-103
agcagcauuguacagggcuauga rno-miR-106b
uaaagugcugacagugcagau rno-miR-107
agcagcauuguacagggcuauca rno-miR-122a
uggagugugacaauggyguuugu rno-miR-124a
uuaaggcacgcggugaaugcca rno-miR-125a
ucccugagacccuuuaaccugug rno-miR-125b
ucccugagacccuaacuuguga rno-miR-126*
cauuauuacuuuugguacgcg TABLE 9-continued

```
rno-miR-126
ucguaccgugaguaauaaugc rno-miR-127
ucggauccgucugagcuuggcu rno-miR-128a
ucacagugaaccggucucuuuu rno-miR-128b
ucacagugaaccggucucuuuc rno-miR-130a
cagugcaauguuaaagggc rno-miR-130b
cagugcaaugaugaaagggcau rno-miR-132
uaacagucuacagccauggucg rno-miR-133a
uugucccuucaaccagcugu rno-miR-134
ugugacugguugaccagaggg rno-miR-135a
uauggcuuuuuauuccuauguga rno-miR-136
acuccauuuguuugaugaugga rno-miR-137
uauugcuuaagaauacgcguag rno-miR-138
agcugguguugugaauc rno-miR-139
ucuacagugcacgugucu rno-miR-141
aacacugucugguaaagaugg rno-miR-142-5
cauaaaguagaaagcacuac rno-miR-142-3p
uguaguguuccuacuuuaugga rno-miR-143
ugagaugaagcacuguagcuca rno-miR-144
uacaguauagaugauguacuag rno-miR-145
guccaguuuucccaggaaucccuu rno-miR-146
ugagaacugaauuccauggguu rno-miR-150
ucucccaacccuuguaccagug rno-miR-152
ucagugcaugacagaacuugg rno-miR-153
uugcauagucacaaaaguga rno-miR-154
uagguuauccguguugccuucg rno-miR-181c
aacauucaaccugucggugagu
```

TABLE 9-continued rno-miR-181a
aacauucaacgcugucggugagu rno-miR-181b
aacauucauugcugucgguggguu rno-miR-183
uauggcacugguagaauucacug rno-miR-184
uggacggagaacugauaagggu rno-miR-185
uggagagaaaggcaguuc rno-miR-186
caaagaauucuccuuuugggcuu rno-miR-187
ucgucuuguguugcagccg rno-miR-190
ugauauguuugauauauuaggu rno-miR-191
caacggaaucccaaaagcagcu rno-miR-192
cugaccuaugaauugacagcc rno-miR-193
aacuggccuacaaagucccag rno-miR-194
uguaacagcaacuccaugugga rno-miR-195
uagcagcacagaaauauuggc rno-miR-196
uagguaguuucauguuguugg rno-miR-199a
cccaguguucagacuaccuguuc rno-miR-200c
aauacugccggguaaugaugga rno-miR-200a
uaacacugucuggaacgaugu rno-miR-200b
cucuaauacugccugguaaugaug rno-miR-203
uccuucauuccaccggagucug rno-miR-204
uucccuuugucuccuaugccu rno-miR-205
uccuucauuccaccggagucug rno-miR-206
uggaauguaaggaagugugugg rno-miR-208
auaagacgagcaaaaagcuugu rno-miR-210
cugugcgugugacagcggcug rno-miR-211
uucccuuugucauccuuugccu rno-miR-212
uaacagucuccagucacggcc TABLE 9-continued rno-miR-213
accaucgaccguugauuguacc rno-miR-214
acagcaggcacagacaggcag rno-miR-216
uaaucucagcuggcaacugug rno-miR-217
uacugcaucaggaacugacuggau rno-miR-218
uugugcuugaucuaaccaugu rno-miR-219
ugauuguccaaacgcaauucu rno-miR-221
agcuacauugucugcuggguuuc rno-miR-222
agcuacaucuggcuacugggucuc rno-miR-223
ugucaguuugucaaauacccc rno-miR-290
cucaaacuauggggcacuuuuu rno-miR-291-5p
caucaaaguggaggcccucucu rno-miR-291-3p
aaagugcuuccacuuugugugcc rno-miR-292-5p
acucaaacuggggcucuuuug rno-miR-292-3p
aagugccgccagguuuugagugu rno-miR-296
agggccccccucaauccugu rno-miR-297
auguaugugugcauguaugcaug rno-miR-298
ggcagaggagggcuguucuucc rno-miR-299
ugguuuaccgucccacauacau rno-miR-300
uaugcaagggcaagcucucuuc rno-miR-320
aaaagcuggguugagagggcgaa rno-miR-321
uaagccagggauuguggguuc Although the disclosed teachings have been described with reference to various applications, methods, kits, and compositions, it will be appreciated that various changes and modifications may be made without departing from the teachings herein. The foregoing examples are provided to better illustrate the disclosed teachings and are not intended to limit the scope of the teachings herein.

We claim:

1. A method for detecting a micro RNA (miRNA), wherein the miRNA is 18-25 ribonucleotides in length, comprising;
   hybridizing the miRNA and a linker probe, wherein the linker probe comprises a stem, a loop, and a 3' target-specific portion, wherein the 3' target-specific portion base pairs with a 3' end region of the miRNA;
   extending the linker probe to form an extension reaction product;
   amplifying the extension reaction product in a polymerase chain reaction comprising a detector probe and a reverse primer that hybridizes to the linker probe or a complementary sequence to the linker probe, to form an amplification product, with the proviso that the linker probe is a different molecule from the detector probe,
   wherein the detector probe hybridizes to a nucleotide of the linker probe stem in the amplification product or hybridizes to a nucleotide of a complementary sequence of the linker probe stem in the amplification product; and,
   detecting the miRNA.

2. The method according to claim 1 wherein the polymerase chain reaction comprises a forward primer that hybridizes to the miRNA or a complementary sequence to the miRNA.

3. The method according to claim 1 wherein the detector probe hybridizes to a nucleotide of the 3' end region of the miRNA in the amplification product or hybridizes to a nucleotide of a complementary sequence to the 3' end region of the miRNA in the amplification product.

4. The method according to claim 1 wherein the detector probe hybridizes to a nucleotide of a region upstream from the 3' end region of the miRNA in the amplification product or hybridizes to a nucleotide of a complementary sequence to a region upstream from the 3' end region of the miRNA in the amplification product.

5. The method according to claim 1 wherein the detector probe is a 5'-nuclease cleavable probe.

6. The method according to claim 5 wherein the 5'-nuclease cleavable probe comprises FAM.

7. The method according to claim 5 wherein the 5'-nuclease cleavable probe comprises VIC.

8. The method according to claim 1 wherein the detector probe comprises peptide nucleic acid (PNA).

9. The method according to claim 8 wherein the PNA probe comprises FAM.

10. The method according to claim 8 wherein the PNA probe comprises VIC.

11. The method according to claim 1 wherein the detector probe comprises locked nucleic acid (LNA).

12. The method according to claim 1 herein the detector probe comprises a universal base.

13. The method according to claim 1 wherein the extending is a reverse transcription reaction comprising a reverse transcriptase.

14. The method according to claim 1 wherein the stem of the linker probe comprises 12-16 base-pairs.

15. The method according to claim 14 wherein the stem of the linker probe comprises 14 base-pairs.

16. The method according to claim 1 wherein the 3' target specific portion of the linker probe comprises 5-8 nucleotides.

17. The method according to claim 1 wherein the loop corresponds to a universal reverse primer portion.

18. The method according to claim 1 wherein the loop comprises 14-18 nucleotides.

19. The method according to claim 18 wherein the loop comprises 16 nucleotides.

20. The method according to claim 1 wherein the Tm of the detector probe is 63-69 C.

21. A method for detecting a target polynucleotide comprising;
   hybridizing the target polynucleotide and a linker probe, wherein the linker probe comprises a stem, a loop, and a 3' target-specific portion, wherein the 3' target-specific portion base pairs with a 3' end region of the target polynucleotide;
   extending the linker probe to form an extension reaction product;
   amplifying the extension reaction product to form an amplification product in the presence of a detector probe, wherein the amplification is a polymerase chain reaction, wherein the amplification comprises a forward primer that hybridizes to the target polynucleotide or a complementary sequence to the target polynucleotide, and a reverse primer that hybridizes to the linker probe or a complementary sequence to the linker probe, wherein the detector probe hybridizes to a nucleotide of the linker probe stem in the amplification product or hybridizes to a nucleotide of a complementary sequence to the linker probe stem in the amplification product with the proviso that the linker probe is a different molecule from the detector probe; and,
   detecting the target polynucleotide.

22. The method according to claim 21 wherein the target polynucleotide is a micro RNA (miRNA).

23. The method according to claim 21 wherein the detector probe hybridizes to a nucleotide of the 3' end region of the target polynucleotide in the amplification product or hybridizes to a nucleotide of a complementary sequence to the 3' end region of the target polynucleotide in the amplification product.

24. The method according to claim 21 wherein the detector probe hybridizes to a nucleotide of a region upstream from the 3' end region of the target polynucleotide in the amplification product or hybridizes to a nucleotide of a complementary sequence to a region up stream from the 3' end region of the target polynucleotide in the amplification product.

25. The method according to claim 21 wherein the detector probe is a 5'-nuclease cleavable probe.

26. The method according to claim 25 wherein the 5'-nuclease cleavable probe comprises FAM.

27. The method according to claim 25 wherein the 5'-nuclease cleavable probe comprises VIC.

28. The method according to claim 21 wherein the detector probe comprises peptide nucleic acid (PNA).

29. The method according to claim 28 wherein the PNA probe comprises FAM.

30. The method according to claim 28 wherein the PNA probe comprises VIC.

31. The method according to claim 21 wherein the detector probe comprises locked nucleic acid (LNA).

32. The method according to claim 21 wherein the detector probe comprises a universal base.

33. The method according to claim 21 the extending is a reverse transcription reaction comprising a reverse transcriptase.

34. The method according to claim 21 wherein the stem of the linker probe comprises 12-16 base-pairs.

35. The method according to claim 34 wherein the stem of the linker probe comprises 14 base-pairs.

36. The method according to claim 21 wherein the 3' target specific portion of the linker probe comprises 5-8 nucleotides.

37. The method according to claim 21 wherein the loop further comprises a universal reverse primer portion.

38. The method according to claim 21 wherein the loop comprises 14-18 nucleotides.

39. The method according to claim 38 wherein the loop comprises 16 nucleotides.

40. The method according to claim 21 wherein the Tm of the detector probe is 63-69 C.

41. A method for detecting a miRNA molecule comprising;
hybridizing the miRNA molecule and a linker probe, wherein the miRNA molecule comprises a 3' end region, wherein the linker probe comprises a stem, a loop, and a 3' target specific portion, wherein the 3' target-specific portion base pairs with the 3' end region of the miRNA molecule;
extending the linker probe to form an extension reaction product;
amplifying the extension reaction product in the presence of a detector probe to form an amplification product, wherein the amplification comprises a polymerase chain reaction, wherein the amplification comprises:
a forward primer that hybridizes to the target polynucleotide or a complementary sequence to the target polynucleotide, and
a reverse primer that hybridizes to the linker probe or a complementary sequence to the linker probe,
wherein the detector probe hybridizes to a nucleotide of the linker probe stem in the amplification product or hybridizes to a nucleotide of a complementary sequence to the linker probe stem in the amplification product, and the detector probe further hybridizes to a nucleotide of the 3' end region of the miRNA in the amplification product or hybridizes to a nucleotide of a complementary sequence to the 3' end region of the miRNA in the amplification product, with the proviso that the linker probe is a different molecule from the detector probe; and,
detecting the miRNA molecule.

42. The method according to claim 41 wherein the miRNA is 18-25 ribonucleotides in length.

43. The method according to claim 41 wherein the detector probe is a 5'-nuclease cleavable probe.

44. The method according to claim 43 wherein the 5'-nuclease cleavable probe comprises FAM.

45. The method according to claim 43 wherein the 5'-nuclease cleavable probe comprises VIC.

46. The method according to claim 41 wherein the detector probe comprises peptide nucleic acid (PNA).

47. The method according to claim 46 wherein the PNA probe comprises FAM.

48. The method according to claim 46 wherein the PNA probe comprises VIC.

49. The method according to claim 41 wherein the detector probe comprises locked nucleic acid (LNA).

50. The method according to claim 41 wherein the detector probe comprises a universal base.

51. The method according to claim 41 wherein the extending is a reverse transcription reaction comprising a reverse transcriptase.

52. The method according to claim 41 wherein the stem of the linker probe comprises 12-16 base-pairs.

53. The method according to claim 52 wherein the stem of the linker probe comprises 14 base-pairs.

54. The method according to claim 41 wherein the 3' target specific portion of the linker probe comprises 5-8 nucleotides.

55. The method according to claim 41 wherein the loop further comprises a universal reverse primer portion.

56. The method according to claim 41 wherein the loop comprises 14-18 nucleotides.

57. The method according to claim 56 wherein the loop comprises 16 nucleotides.

58. The method according to claim 41 wherein the Tm of the detector probe is 63-69 C.

59. A method for detecting two different miRNAs from a single hybridization reaction comprising;
hybridizing a first miRNA and a first linker probe, and a second miRNA and a second linker probe, wherein the first linker probe and the second linker probe each comprise a loop, a stem, and a 3' target-specific portion, wherein the 3' target-specific portion of the first linker probe base pairs with a 3' end region of the first miRNA, and wherein the 3' target-specific portion of the second linker probe base pairs with a 3' end region of the second miRNA;
extending the first linker probe and the second linker probe to form extension reaction products;
dividing the extension reaction products into a first amplification reaction vessel to form a first amplification reaction product, and a second amplification reaction vessel to form a second amplification reaction product, wherein within the first amplification reaction vessel is a first polymerase chain reaction vessel and within the second amplification reaction vessel is a second polymerase chain reaction vessel, wherein the first polymerase chain reaction vessel comprises a forward primer that hybridizes to the first miRNA or a complementary sequence to the first miRNA, and a reverse primer that hybridizes to the linker probe or a complementary sequence to the linker probe, wherein the second polymerase chain reaction vessel comprises a forward primer that hybridizes to the second miRNA or a complementary sequence to the second miRNA, and a reverse primer that hybridizes to the linker probe or a complementary sequence to the linker probe,
wherein a primer in the first amplification reaction vessel hybridizes to the first miRNA, or a complementary sequence to the first miRNA, and not the second miRNA, and a primer in the second amplification reaction vessel hybridizes to the second miRNA, or a complementary sequence to the first miRNA, and not the first miRNA,
wherein a first detector probe in the first amplification reaction vessel differs from a second detector probe in the second amplification reaction vessel, with the proviso that the first linker probe is a different molecule from the first detector probe and the second linker probe is a different molecule from the second detector probe;
wherein the first detector probe hybridizes to a nucleotide of the first linker probe stem of the amplification product or hybridizes to a nucleotide of a complementary sequence to the first linker probe stem in the first amplification product,
wherein the second detector probe hybridizes to a nucleotide of the second linker probe stem of the amplification product or hybridizes to a nucleotide of a complementary sequence to the second linker probe stem in the amplification product; and,
detecting the two different miRNAs.

60. The method according to claim 59 wherein the reverse primer in the first polymerase chain reaction vessel and the reverse primer in the second polymerase chain reaction vessel are a universal reverse primer.

61. The method according to claim 59 wherein the first miRNA and/or the second miRNA is 18-25 ribonucleotides in length.

62. The method according to claim 59 wherein the first detector probe and/or the second detector probe is a 5'-nuclease cleavable probe.

63. The method according to claim 62 wherein the first detector probe and/or the second detector probe comprises FAM.

64. The method according to claim 62 wherein the first detector probe and/or the second detector probe comprises VIC.

65. The method according to claim 59 wherein the first detector probe and/or the second detector probe comprises peptide nucleic acid (PNA).

66. The method according to claim 65 wherein first detector probe and/or the second detector probe comprises FAM.

67. The method according to claim 65 wherein the first detector probe and/or the second detector probe comprises VIC.

68. The method according to claim 59 wherein the first detector probe and/or the second detector probe comprises locked nucleic acid (LNA).

69. The method according to claim 59 wherein the first detector probe and/or the second detector probe comprises a universal base.

70. The method according to claim 59 wherein the extending is a reverse transcription reaction comprising a reverse transcriptase.

71. The method according to claim 59 wherein the stem of the first linker probe and/or the second linker probe comprises 12-16 base-pairs.

72. The method according to claim 71 wherein the stem of the first linker probe and/or the second linker probe comprises 14 base-pairs.

73. The method according to claim 59 wherein the 3' target specific portion of the first linker probe and/or the second linker probe comprises 5-8 nucleotides.

74. The method according to claim 59 wherein the loop of the first linker probe and/or the second linker probe further comprises a universal reverse primer portion.

75. The method according to claim 59 wherein the loop of the first linker probe and/or the second linker probe comprises 14-18 nucleotides.

76. The method according to claim 75 wherein the loop of the first linker probe and/or the second linker probe comprises 16 nucleotides.

77. The method according to claim 59 wherein the Tm of the first detector probe and/or the second detector probe is 63-69 C.

78. A method for detecting two different target polynucleotides from a single hybridization reaction comprising;
hybridizing a first target polynucleotide and a first linker probe, and a second target polynucleotide and a second linker probe, wherein the first linker probe and the second linker probe each comprise a loop, a stem, and a 3' target-specific portion, wherein the 3' target-specific portion of the first linker probe base pairs with a 3' end region of the first target polynucleotide, wherein the 3' target-specific portion of the second linker probe base pairs with a 3' end region of the second target polynucleotide, wherein the first target polynucleotide is 18 to 25 nucleotides in length, and wherein the second target polynucleotide is 18 to 25 nucleotides in length;
extending the first linker probe and the second linker probe to form extension reaction products;
dividing the extension reaction products into a first amplification reaction vessel to form a first amplification reaction product in the presence of a first detector probe and a second amplification reaction vessel to form a second amplification reaction product in the presence of a second detector probe, with the proviso that the first linker probe is a different molecule from the first detector probe, and the second liner probe is a different molecule from the second detector probe, wherein within the first amplification reaction vessel is a first polymerase chain reaction and within the second amplification reaction vessel is a second polymerase chain reaction;
wherein the first polymerase chain reaction comprises a forward primer that hybridizes to the first target polynucleotide or a complementary sequence to the first target polynucleotide, and a reverse primer that hybridizes to the linker probe or a complementary sequence to the linker probe,
wherein the second polymerase chain reaction comprises a forward primer that hybridizes to the second target polynucleotide or a complementary sequence to the second target polynucleotide, and a reverse primer that hybridizes to the linker probe or a complementary sequence to the second linker probe; and,
detecting the first target polynucleotide and the second target polynucleotide, wherein the first detector probe hybridizes to a nucleotide of the first linker probe in the first amplification product or hybridizes to a nucleotide of a complementary sequence to the first linker probe in the first amplification product, and/or the second detector probe hybridizes to a nucleotide of the second linker probe in the second amplification product or hybridizes to a nucleotide of a complementary sequence to the second linker probe in the second amplification product.

79. The method according to claim 78 wherein the reverse primer in the first polymerase chain reaction and the reverse primer in the second polymerase chain reaction are a universal reverse primer.

80. The method according to claim 78 wherein the target polynucleotide is a micro RNA (miRNA).

81. The method according to claim 78 wherein the first amplification reaction vessel comprises a first detector probe and/or the second amplification reaction vessel comprises a second detector probe.

82. The method according to claim 81 wherein the first detector probe hybridizes to a nucleotide of the first linker probe stem of the first amplification product or hybridizes to a nucleotide of a complementary sequence to the first linker probe stem in the first amplification product, and/or the second detector probe hybridizes to a nucleotide of the second linker probe stem in the second amplification product or hybridizes to a nucleotide of a complementary sequence to the second linker probe stem in the second amplification product.

83. The method according to claim 81 wherein the first detector probe hybridizes to a nucleotide of the 3' end region of the first target polynucleotide in the first amplification product or hybridizes to a nucleotide of a complementary sequence to the 3' end region of the first target polynucleotide in the first amplification product, and/or the second detector probe hybridizes to a nucleotide of the 3' end region of the second target polynucleotide in the second amplification product or hybridizes to a nucleotide of a complementary sequence to the 3' end region of the second target polynucleotide in the second amplification product.

84. The method according to claim 81 wherein the first detector probe hybridizes to a nucleotide of a region upstream from the 3' end region of the first target polynucleotide in the first amplification product or hybridizes to a nucleotide of a complementary sequence to a region upstream from the 3' end region of the first target polynucleotide in the first amplification product, and/or the second detector probe hybridizes to a nucleotide of a region upstream from the 3' end region of the second target polynucleotide in the second amplification product or hybridizes to a nucleotide of a complementary sequence to a region upstream from the 3' end region of the second target polynucleotide in the second amplification product.

85. The method according to claim 78 wherein the first target polynucleotide and/or the second target polynucleotide is 18-25 ribonucleotides in length.

86. The method according to claim 81 wherein the first detector probe and/or second detector probe is a 5'-nuclease cleavable probe.

87. The method according to claim 86 wherein the first detector probe and/or second detector probe comprises FAM.

88. The method according to claim 86 wherein the first detector probe and/or second detector probe comprises VIC.

89. The method according to claim 81 wherein the first detector probe and/or second detector probe comprises peptide nucleic acid (PNA).

90. The method according to claim 89 wherein first detector probe and/or second detector probe comprises FAM.

91. The method according to claim 89 wherein the first detector probe and/or second detector probe comprises VIC.

92. The method according to claim 81 wherein the first detector probe and/or the second detector probe comprises locked nucleic acid (LNA).

93. The method according to claim 81 wherein the first detector probe and/or the second detector probe comprises a universal base.

94. The method according to claim 78 wherein the extending is a reverse transcription reaction comprising a reverse transcriptase.

95. The method according to claim 78 wherein the stem of the first linker probe and/or the second linker probe comprises 12-16 base-pairs.

96. The method according to claim 95 wherein the stem of the first linker probe and/or the second linker probe comprises 14 base-pairs.

97. The method according to claim 78 wherein the 3' target specific portion of the first linker probe and/or the second linker probe comprises 5-8 nucleotides.

98. The method according to claim 78 wherein the loop of the first linker probe and/or the second linker probe comprises a universal reverse primer portion.

99. The method according to claim 78 wherein the loop of the first linker probe and/or the second linker probe comprises 14-18 nucleotides.

100. The method according to claim 99 wherein the loop of the first linker probe and/or the second linker probe comprises 16 nucleotides.

101. The method according to claim 81 wherein the Tm of the first detector probe and/or second detector probe is 63-69 C.

102. A method for detecting a miRNA molecule from a cell lysate comprising;
hybridizing the miRNA molecule from the cell lysate with a linker probe,
wherein the linker probe comprises a stem, a loop, and a 3' target specific portion, wherein the 3' target-specific portion base pairs with a 3' end region of the miRNA;
extending the linker probe to form an extension reaction product;
amplifying the extension reaction product to form an amplification product in the presence of a detector probe, wherein the detector probe simultaneously hybridizes to both a) a nucleotide of the linker probe stem of the amplification product or hybridizes to a nucleotide of a complementary sequence to the linker probe stem in the amplification product, and b) a nucleotide of the 3' end region of the miRNA in the amplification product or hybridizes to a nucleotide of a complementary sequence to the 3' end region of the miRNA in the amplification product, with the proviso that the linker probe is a different molecule from the detector probe; and,
detecting the miRNA molecule.

103. The method according to claim 102, wherein the cell lysate comprises;
treating cells with a lysis buffer, wherein the lysis buffer comprises,
10 mM Tris-HCl, pH 8.0;
0.02% Sodium Azide; and,
0.03% Tween-20.

104. A method for detecting a RNA, wherein the RNA is 18-25 ribonucleotides in length, comprising;
hybridizing the RNA and a linker probe, wherein the linker probe comprises a stem, a loop, and a 3' target-specific portion, wherein the 3' target-specific portion base pairs with a 3' end region of the RNA;
extending the linker probe to form an extension reaction product;
amplifying the extension reaction product in a polymerase chain reaction comprising a detector probe to form an amplification product, wherein the detector probe simultaneously hybridizes to both a) a nucleotide of the linker probe stem of the amplification product or hybridizes to a nucleotide of a complementary sequence to the linker probe stem in the amplification product, and b) a nucleotide of the 3' end region of the RNA in the amplification product or hybridizes to a nucleotide of a complementary sequence to the 3' end region of the RNA in the amplification product; and,
detecting the RNA.

* * * * *